United States Patent [19]
Ning

[11] Patent Number: 6,075,836
[45] Date of Patent: Jun. 13, 2000

[54] METHOD OF AND SYSTEM FOR INTRAVENOUS VOLUME TOMOGRAPHIC DIGITAL ANGIOGRAPHY IMAGING

[75] Inventor: Ruola Ning, Penfield, N.Y.

[73] Assignee: University of Rochester, Rochester, N.Y.

[21] Appl. No.: 09/014,107

[22] Filed: Jan. 27, 1998

Related U.S. Application Data

[63] Continuation-in-part of application No. 08/888,331, Jul. 3, 1997.

[51] Int. Cl.$^7$ ................................. A61B 6/00; A61B 6/03
[52] U.S. Cl. ........................ 378/98.12; 378/17; 378/901
[58] Field of Search ............................. 378/4, 17, 98.11, 378/98.12, 901

[56] References Cited

U.S. PATENT DOCUMENTS

| | | |
|---|---|---|
| 5,257,183 | 10/1993 | Tam . |
| 5,365,560 | 11/1994 | Tam . |
| 5,390,226 | 2/1995 | Tam . |
| 5,461,650 | 10/1995 | Tam . |
| 5,671,265 | 9/1997 | Andress ................................ 378/98.11 |
| 5,802,133 | 9/1998 | Kawai et al. ................................ 378/4 |

OTHER PUBLICATIONS

Bruce D. Smith, "Image Reconstruction from Cone–Beam Projections: Necessary and Sufficient Conditions and Reconstruction Methods" IEEE Transactions on Medical Imaging, vol. M1–4, No. 1, Mar. 1985, pp 14–25.

Primary Examiner—David V. Bruce
Attorney, Agent, or Firm—Blank Rome Comisky & McCauley LLP

[57] ABSTRACT

A method of and system for performing intravenous tomographic digital angiography imaging which combines the principles of intravenous digital angiography with those of cone-beam volume tomography for generating a direct, unambiguous and accurate 3-D reconstruction of stenosis and other irregularities and malformations from 2-D cone-beam tomography projections is disclosed in which several different data acquisition geometries, such as a circle-plus-arc data acquisition geometry, may be utilized to provide a complete set of data so that an exact 3-D reconstruction is obtained. Only a single IV contrast injection with a short breathhold by the patient is needed for use with a volume CT scanner which uses a cone-beam x-ray source and a 2-D detector for fast volume scanning in order to provide true 3-D descriptions of vascular anatomy with more than 0.5 lp/mm isotropic resolution in the x, y and z directions is utilized in which one set of cone-beam projections is acquired while rotating the x-ray tube and detector on the CT gantry and then another set of projections is acquired while tilting the gantry by a small angle. The projection data is preweighted and the partial derivatives of the preweighted projection data are calculated. Those calculated partial derivatives are rebinned to the first derivative of the Radon transform, for both the circular orbit data and the arc orbit data. The second partial derivative of the Radon transform is then calculated and then the reconstructed 3-D images are obtained by backprojecting using the inverse Radon transform.

47 Claims, 4 Drawing Sheets

METHOD OF AND SYSTEM FOR INTRAVENOUS VOLUME TOMOGRAPHIC DIGITAL ANGIOGRAPHY IMAGING

CROSS REFERENCE TO RELATED APPLICATION

This application is a continuation-in-part of U.S. patent application Ser. No. 08/888,331, filed Jul. 3, 1997, entitled "METHOD OF AND SYSTEM FOR CONE-BEAM TOMOGRAPHY RECONSTRUCTION, which is commonly assigned herewith.

BACKGROUND OF THE INVENTION

The present invention is directed to a method of and system for computed tomography (CT) density image reconstruction. More particularly, the present invention is directed to the three-dimensional reconstruction from two-dimensional projections acquired with x-ray cone-beam CT and single photon emission computed tomography (SPECT) scanners. Even more particularly, the present invention is directed to a method of and system for intravenous volume tomographic digital angiography imaging.

For about the past twenty years, computerized tomography has revolutionized diagnostic imaging systems as well as non-destructive test imaging techniques. Conventional CT scanners use a fan-shaped x-ray beam and one-dimensional detector in order to reconstruct a single slice with a single scan of an object. However, current CT technology is limited by a trade-off between high longitudinal resolution and fast volume scanning. One method which has been utilized to address the shortcomings of CT scanner technology is the use of cone-beam tomography. A cone-beam volume CT scanner uses a cone-beam x-ray source and a two-dimensional detector to reconstruct the whole volume of an object with a single scan of that object. The data obtained from the scan of the object is processed in order to construct an image that presents a two-dimensional slice taken through the object. The current technique for reconstructing an image from 2-D is referred to in the art as the filtered back projection technique. That process converts the attenuation measurements from a scan into integers called "CT numbers" or "Hounsfield units" which are then used to control the brightness of a corresponding pixel on a cathode ray display.

In a 3-D scan technique, a cone-shaped x-ray beam is used which diverges to form a cone-beam that passes through the object and impinges on a two-dimensional array of detector elements. In that manner, the volume scanning time of a 3-D object can be at least 10 times shorter than a standard CT on a spiral CT. In contrast to existing CT with an intraslice plane resolution of 1.0 lp/mm, the reconstructions of cone beam CT will have isotropic spatial resolution along all three axes (0.5–2.0 lp/mm). Each view is thus a 2-D array of x-ray attenuation measurements and the complete scan produces a 3-D array of attenuation measurements.

At present, either of two methods are commonly used to reconstruct a set of images from the acquired 2-D attenuation measurements. The first technique is that developed by Feldkamp, Davis & Kress, which is described in "Practical Cone-Beam Algorithm", *J. Opt. Soc. Am.*, Vol. I, pp. 612–619 (1984). The Feldkamp, et al. technique, which uses an algorithm which was derived using approximations of a tilted fan beam formula, is a convolution-back projection method which operates directly on the line integrals of the actual attenuation measurements. That method can be easily implemented with currently available hardware and is a good reconstruction for images at the center or "mid-plane" of the cone-beam. While the algorithm of Feldkamp, et al. provides excellent computational efficiency and minimal mechanical complexity in data acquisition, its major shortcoming is that it is based on single circle cone-beam geometry. Single circle cone-beam geometry, in which the source always lies on a circle, cannot provide a complete set of data to exactly reconstruct the object. For that reason, Feldkamp, et al.'s algorithm causes some unavoidable distortion in the non-central transverse planes, as well as resolution degradation in the longitudinal direction.

In order to address the problems of Feldkamp's algorithm, several other approaches have been proposed using different cone-beam geometries including dual orthogonal circles, helical orbit, orthogonal circle-and-line, and Smith's curve. Such geometries can achieve exact reconstructions when using the approach of Tuy, Smith, or Gangreat.

In addition to the Feldkamp, et al. approach for analytic cone-beam reconstruction, a second commonly used method is that disclosed by Pierre Grangeat in, "Mathematical Framework of Cone-Beam 3-D Reconstruction Via the First Derivative of the Radon Transform", *Mathematical Methods in Tomography*, Herman, Lewis, Natterer (eds.) Lecture Notes in Mathematics, No. 1497, pp. 66–97, Spring Verlag (1991). That algorithm provides an accurate solution to the image reconstruction task based on a fundamental relationship between the derivative of the cone-beam plane integral through the derivative of the parallel beam plane integral. While the Grangeat method is theoretically accurate, it requires mathematical operations that can be solved only using finite numerical calculations that are approximations. Thus, errors can be introduced by the implementation of the Grangeat method that can be greater than those produced using the Feldkamp, et al. method and such errors are not correlated with the cone-beam angle.

A third method has been disclosed by H. K. Tuy in "An Inversion Formula for a Cone-Beam Reconstruction", *SAIM J. Appl. Math.* 43, pp. 546–552 (1983). Using Tuy's approach, in order to generate a complete or sufficient set of data, every plane which passes through the imaging field of view must also cut through the orbit of the focal point at least once. The single plane or orbit of Feldkamp, et al. does not satisfy this condition.

Still yet another approach that has been proposed is the inversion of the cone-beam data sets if the assumption is made that for any line that contains a vertex point and a reconstruction point, there is an integer M which remains constant for the line such that almost every plane that contains this line intersects the geometry exactly M times. Mathematical improvement to the reconstruction algorithms was described in an article by B. D. Smith entitled "Cone-Beam Tomography: Recent Advances and a Tutorial Review," *Opt. Eng.*, Vol. 29 (5) pp. 524–534 (1990). However, such an integer requirement condition is too restrictive for practical application since the only known source point geometry which meets that condition is a straight line.

Two somewhat recent patents were issued in the United States directed to the cone-beam reconstruction problem. The first, U.S. Pat. No. 5,170,439 to Zeng, et al., was issued on Dec. 8, 1992 and utilizes the above-described cone-beam reconstruction method using combined circle and line orbits. However, that technique requires the removal of redundant and unnecessary data, which necessarily requires more computing time and complexity than the method and system of the present invention.

Another approach to the reconstruction of images from cone-beam data is disclosed in U.S. Pat. No. 5,400,255, which issued to Hu on Mar. 21, 1995. The methodology disclosed in the Hu patent represents a minimal improvement from Feldkamp's algorithm and it is still an approximate method based on a single circle cone beam geometry. It cannot result in exact reconstruction and it is not acceptable in many clinical applications when the cone angle is large.

In contrast to the prior art approaches, the present invention discloses an exact cone-beam reconstruction system and method using a circle-plus-arc data acquisition geometry in which the locus of a source and a detector is a circle plus an orthogonal arc. In that manner, the best image quality of a cone-beam volume CT is achieved without introducing any additional mechanical complexity compared to a regular CT gantry. If the locus of an x-ray source and a detector is a single circle during cone-beam scanning (single circle cone-beam geometry), an incomplete set of projection data will be acquired. The incompleteness of the projection data results in some unavoidable blurring in the planes away from the central z plane and a resolution loss in the z direction (i.e., Feldkamp, et al.'s algorithm). The reconstruction error due to the incompleteness of the projection data could be up to 50% of the signal when using Feldkamp, et al.'s algorithm with a 22° cone angle. However, using the data acquisition geometry of the present invention, the locus of an x-ray source and a detector is a circle plus an arc perpendicular to the circle. That corresponds to rotating the x-ray tube and detector on the gantry, and then acquiring the arc projections on a perpendicular arc while tilting the gantry at a relatively small angle (±15° to ±30°). Such geometry results in a complete set of data for an object with a 25–40 cm length in the z direction, which corresponds to a 37–60 cm field size at the detector in the z direction with a magnification of 1.5. Using the system and method of the present invention, the 3-D reconstruction is exact and no image blurring or resolution loss occurs.

The method and system of the present invention is based upon the three-dimensional Radon transform. The algorithm used with the present invention first transforms the cone-beam projections acquired from a circle-arc orbit into the first derivative of the 3-D Radon transform of an object using Grangeat's formula. Then, the object function is reconstructed using the inverse Radon transform. In order to reduce the interpolation errors in the re-binning process required by Grangeat's formula, new re-binning equations have been derived exactly, therefore transforming 3-D interpolations into one-dimensional interpolations. The inventive cone-beam acquisition method and system disclosed herein provides a complete set of projection data such that the cone-beam image reconstruction algorithm achieves exact reconstructions. The result is a 3-D cone-beam reconstruction which introduces no obvious artifacts and only a practical acceptable reduction of reconstruction accuracy.

The 3-D volume tomographic imaging and system described above can also be used to achieve a 3-D or volume tomographic digital angiography imaging method and system which is capable of providing clinically useful 3-D vascular images for enhancing diagnostic and therapeutic decisions. In particular, the volume tomographic digital angiography imaging method and system disclosed herein is particularly useful for intravenous (IV) volume tomographic digital angiography (IV-VTDA). Such IV-VTDA is superior to conventional angiography because it provides a direct, unambiguous and accurate 3-D measurement of stenosis and other irregularities and malfunctions, including the caliber, geometry and spatial orientation in the structure. Moreover, the IV-VTDA method and system disclosed herein requires only a single IV injection of contrast media and uses fast volume scanning, thus reducing the invasiveness of the procedure as well as the procedure time, while also providing a substantial reduction in the total x-ray exposure to the patient.

A need for the accurate and detailed assessment of atherosclerotic disease has been reemphasized by the growth of new therapeutic techniques, such as thrombolysis, endarterectomy, atherectomy, angioplasty, embolization and the placement of vascular stents, as well as the need to facilitate and improve the success rate of such therapeutic procedures. Cerebrovascular disease is the third leading cause of death in the United States and claims approximately 500,000 new victims each year. New surgical and endovascular techniques greatly improve patient survival and their quality of life. Thus, there has been an increase in the therapeutic procedures enumerated above in the last several years. As the result of such procedures, patient survival has increased and the quality of the patient's life has improved.

The identification of patients who can benefit from a specific therapeutic procedure requires both accurate and detailed information about the severity of the stenosis, their geometry and their spatial orientation. However, most therapeutic decisions are based on information obtained through standard projectional angiographic techniques. Projection images using such standard projectional techniques do not provide sufficient information with which to detect and completely characterize all vascular lesions. That lack of complete data impairs the ability of the physician to determine the optimal therapeutic procedure. Obviously, an inappropriate choice of intervention based on improper knowledge of the patient's anatomy can lead to unnecessary interventions, a sub-optimal outcome, injury or death.

As discussed above, all of the standard projectional angiographic techniques contain major shortcomings with respect to providing a complete characterization of vascular lesions. For example, intraarterial (IA) digital subtraction angiography (IA-DSA), which is currently used for examining most patients for vascular disease, has two principle limitations. First, IA-DSA provides only a 2-D projection of 3-D anatomical structures. Second, IA-DSA images are of reduced usefulness due to vessel overlap, particularly when non-selective injections are used. Obviously, the knowledge of the geometry of the stenosis and the spatial orientation of the arteries is a major step in the performance of successful surgical or transvascular interventional procedures. Thus, using IA-DSA techniques, multiple views are utilized to attempt to detect all lesions as well as to evaluate the geometry of the stenosis and to integrate the 2-D views into correct spatial relationships. That, in turn, requires the use of multiple contrast injections as well as a multiple series of x-ray exposures.

However, even with multiple views, the number of views is limited, which often results in non-detected lesions because of the failure to achieve orthogonal projection and overlap. Consequently, the angiographic procedure can become prolonged, increasing patient morbidity from lengthened catheterization time, increasing contrast as well as the radiation dose, while also increasing procedure costs. There is also an added risk of complications related to percutaneous cannulation of an artery and the manipulation of the IA catheters and wires in critical vessels which are often affected by vascular disease. The risk of procedure related vascular injury and stroke is also present, with major morbidity. Moreover, such angiography technique is frequently repeated as the vascular disease progresses, thus multiplying costs and risks.

In the past, in order to avoid the shortcomings and risks of IA-DSA, attempts have been made to utilize intravenous digital subtraction angiography (IV-DSA). However, in addition to the shortcomings inherent with all types of DSA, there are two additional important technical deficiencies which are specific to IV-DSA. First, image misregistration often occurs due to patient motion. Such misregistration too often masks the vascular anatomy to be imaged. Second, there is an inability to attain a sufficiently high concentration of contrast media through intravenous injection to overcome the quantum noise inherent in the DSA technique. Due to those deficiencies, the resulting image is generally of poor quality and, thus, IV-DSA has become an infrequently used clinical technique.

In the past fifteen years, many attempts have been made to improve the image quality of IV-DSA. Such techniques have been only partially successful in reducing the severity of motion artifacts and in improving problems with vessel overlaps. Thus, even with such improved IV-DSA techniques, there still exists a significant amount of missing 3-D information which would be very useful to obtain.

An improvement over IA-DSA can be obtained by incorporating the volume tomographic imaging principles discussed herein with digital angiography. As is disclosed in more detail herein, a cone-beam volume CT scanner using an image intensifier coupled to a CCD camera as a 2-D detector can be used to obtain CT-like 3-D reconstructions of blood vessels from a single IA contrast media injection and a single fast volume scan. In contrast to the DSA technique, such an image intensifier-based volume based tomographic imaging method and system provides the ability to tomographically isolate an object of interest, such as a blood vessel, from the structures in an adjacent plane, such as other blood vessels or bone. The 3-D reconstructions eliminate vessel overlap and provide a complete, true 3-D description of the vascular anatomy. Such reconstructions have isotropic spatial resolution along all three axes. Others have reported similar results on selective intra-arterial volume tomographic angiography reconstructions, thus demonstrating the advantages of IA-VTDA over IA-DSA. See, for example, an article entitled "3 D computed x-ray angiography: first in vivo results," by D. St-Felix, R. Campagnalo and Y. Rolland, et al. in *Radiology* 1992, 185:304, a paper presented by R. Fahrig, A. J. Fox and D. W. Haldsworth, entitled "Three-Dimensional CT Angiography from a C Arm Mounted XRII," which was presented at RSNA 82nd Scientific Assembly, Dec. 1, 1996, and a paper presented by K. Sekihara, H. Kawai, K. Yamamoto and T. Kumazaki, entitled "Cone Beam CT Angiography," at *Proc. of JAMIT Frontier'95*, pp. 23–28, 1995.

One of the drawbacks of IA-VTDA is that it is based upon IA injections, which are generally much more invasive than IV injections. Although when compared to DSA, IA-VTDA represents a significant advance, IV-VTDA represents an even greater advance compared to IA-DSA because it has all of the advantages IA-VTDA has over IA-DSA and at the same time makes the angiographic procedure much safer. IV-VTDA also provides a significant reduction in the cost of the angiographic procedure because it eliminates the need for arterial puncture and catherterization.

One of the difficulties of using IV-VTDA in place of IA-VTDA is that IV injections result in a much lower signal compared to IA injections. Whereas a selective IA injection results in almost no dilution of injected iodine concentration and a non-selective IA injection results in a factor of 3–4 dilution, the dilution of central and peripheral IV injections depends on cardiac output, transit time, venous capacitance, the injection rate and the length of the injection. Dilution factors on the order of 20:1–30:1 are common. The result is that an IV-VTDA system must compensate for a significantly lower signal compared to IA-VTDA, which in turn requires that the IV-VTDA system have a much better low contrast resolution than an IA-VTDA system.

There are two IV injection protocols. One is the central IV injection which is performed at the vena cava near the right atrium. The other is the peripheral IV injection, which is performed through the antecubital fossa or other peripheral veins. If necessary, veins in both antecubital fossae can be injected simultaneously to achieve even higher rates of contrast administration intravenously. The injection can be performed using an injector, and contrast solution can be iodinated contrast materials.

Other modalities could potentially also be used for 3-D angiographic imaging, such as helical CT, magnetic resonance angiography (MRA) and ultrasound (US). However, IV-VTDA is clearly preferable to all three of these modalities.

Spiral CT angiography (CTA), while having proven useful for the evaluation of cerebrovascular and aorto iliac disease, has some major disadvantages when compared to IV-VTDA. First, the long volume scan time of CTA limits the rate of contrast injection and at least a 30 second breathhold is required by the patient. Therefore, CTA is more sensitive to patient motion than IV-VTDA techniques. Also, due to tube loading limitations, the resolution in the section direction of CTA is practically limited, and small-vessel resolution may be limited by partial volume effects. IV-VTDA, on the other hand, requires a much shorter volume scanning time, which allows a higher contrast media injection rate so that a much higher IV injected iodine signal can be achieved, which produces a better image quality, requires less contrast media and a much smaller tube loading. Thus, compared to CTA techniques, IV-VTDA can cover a much larger segment of the body in the direction orthogonal to the slices than conventional CTA, with a single injection.

It is contemplated that the use of IV-VTDA for imaging a patient's body will produce significant benefits over the images produced by the present CTA techniques. IV-VTDA is also superior for cross-sectional pulmonary angiography because of its shorter breathhold requirements as well as the isotropic resolution it attains. Furthermore, IV-VTDA can also be used for lower extremity angiography where spiral CTA cannot be used because of the limited tube capacity and total amount of contrast media which can be safely administered to a patient.

MRA has already proven useful for the evaluation of vascular disease. However, current MRA procedures have some deficiencies, including limited spatial resolution, over-estimation of stenosis and other artifacts, particularly at regions of flow disturbances, tradeoffs between maximizing the field of view (FOV), signal to noise ratio and spatial resolution and relatively long scanning times, which make it sensitive to patient motion. While many attempts have been made to solve these problems, even if they are finally solved, the IV-VTDA system and method of the present invention will be less expensive. IV-VTDA can also be used for patients with contraindications to MR scanning, such as claustrophobia, pacemakers, cerebral aneurysm clips, implanted defibrillators, previous surgery with metal implants, or prior trauma with residual metal fragments, and will also allow visualization inside metallic endovascular stents.

Transcutaneous duplex ultrasound (US) has the advantages of real-time non-invasive imaging that provides spectral information in a relatively inexpensive package while also providing extraluminal information. However, compared to IV-VTDA, a principle limitation of ultrasound is the need for an appropriate acoustic window. Intervening air or bone prevent the acquisition of diagnostic information at a substantial number of potential vascular sites. For that reason, ultrasound has a primary diagnostic role in the carotid and lower extremity arteries, but is not useful in adult (closed fontanelle) skull and central chest areas and is limited in use in the deep abdomen. Furthermore, calcific plaque obscures visualization, often right at the stenosis. Other disadvantages of ultrasound include a limited FOV, dependence on Doppler angle, dependence on operator skill, and the inability to distinguish total occlusion from severe stenosis as well as a poor 3-D depiction of the anatomy for surgical planning.

SUMMARY AND OBJECTS OF THE INVENTION

In view of the foregoing, it should be apparent that there still exists a need in the art for a method of and apparatus for producing a 3-D image from two dimensional projections acquired with x-ray cone-beam volume CT and SPECT scanners such that exact reconstructions with no image blurring or distortion are produced. It is, therefore, a primary object of this invention to provide a method of and apparatus for obtaining an exact 3-D reconstruction from 2-D projections acquired with cone-beam volume CT and SPECT scanners which is characterized by lack of image blurring and distortion.

More particularly, it is an object of this invention to provide a new method for cone-beam reconstruction using a circle-plus-arc data acquisition geometry to provide a complete set of data such that an exact 3-D reconstruction can be obtained using a cone-beam x-ray source and a 2-D detector with a conventional CT scanner gantry.

Still more particularly, it is an object of this invention to provide for a circle-plus-arc data acquisition geometry for use with volume CT scanner using a cone-beam x-ray source and a 2-D detector in which a standard CT gantry is utilized without introducing mechanical complexity to achieve exact 3-D reconstructions of an object.

Briefly described, these and other objects of the invention are accomplished by the use of a new analytic cone-beam reconstruction algorithm which uses a circle-plus-arc data acquisition geometry to provide a complete set of data so that an exact 3-D reconstruction is obtained even in cases where Feldkamp's algorithm fails severely. The novel data acquisition scheme disclosed herein is applied to a volume CT scanner which uses a cone-beam x-ray source and a 2-D detector, such as a selenium or silicon thin-film flat-panel x-ray imager. The circle-plus-arc data acquisition scheme is implemented by acquiring one set of cone-beam projections while rotating an x-ray tube and a detector on a standard CT gantry and, then, acquiring another set of projections while tilting the gantry by a small angle of approximately ±15° to approximately ±30° with the x-ray tube and the detector fixed on the gantry. That scanning method is accomplished on a standard CT gantry without introducing mechanical complexity and achieves exact 3-D reconstructions of an object with a 25–40 cm diameter.

In practice, the arc length and arc sampling rate can be reduced (for example, by 50%) without the introduction of any obvious artifacts and with only a practically acceptable reduction of reconstruction accuracy. Thus, data acquisition time on the arc is significantly reduced by decreasing the arc length or arc sampling rate with the result that the desired 3-D image reconstruction may be computed in less time.

In its method aspects, the present invention is carried out by first obtaining the cone-beam projection data from a volume CT or SPECT scanner. Then, that projection data is preweighted and the partial derivatives of the preweighted projection data are calculated. Next, the calculated partial derivatives are rebinned to the first derivative of the Radon transform, for both the circular orbit data and the arc orbit data. The second partial derivative of the Radon transform is then calculated. Finally, the reconstructed 3-D images are obtained by backprojecting using the inverse Radon transform.

In view of the foregoing discussion concerning the need for an accurate assessment of atherosclerotic disease and the limitations of the current techniques for examining most patients for vascular disease, it should be apparent that there still also exists a need in the art for a method of and apparatus for producing a 3-D image of vascular anatomy utilizing IV injections and a volume tomographic digital angiography imaging system which uses an x-ray cone-beam volume CT scanner. It is, therefore, a primary object of this invention to provide a method of and apparatus for obtaining an exact 3-D vascular image for enabling diagnostic and therapeutic decisions using intravenous volume tomographic digital angiography.

More particularly, it is an additional object of this invention to provide a method of and system for using cone-beam volume CT techniques to produce direct, unambiguous and accurate 3-D measurement of stenosis and other irregularities and malformations associated with vascular disease which requires only a single IV injection of contrast media, thus reducing the invasiveness of the procedure.

Still more particularly, it is an object of this invention to provide a method of and system for intravenous volume tomographic digital angiography in which a direct, unambiguous and accurate 3-D measurement of vascular disease is obtained using an x-ray cone-beam volume CT scanner, thus reducing the procedure time while at the same time providing a substantial reduction in the total x-ray exposure to the patient.

Briefly described, these and other objects of the invention are accomplished by the use of an x-ray cone-beam volume CT scanner which utilizes a new analytic cone-beam reconstruction algorithm with a circle-plus-arc data acquisition geometry in order to provide a complete set of data so that an exact 3-D image of the vascular diseased anatomy is obtained with the use of only a single IV injection of contrast medium. The novel IV volume tomographic digital angiography method and apparatus disclosed herein is accomplished using a volume CT scanner which uses a cone-beam x-ray source and a 2-D detector, such as a selenium silicon thin-film flat panel x-ray imager which achieves high resolution, high frame rate and a high dynamic range while at the same time having only a small image lag and excellent linearity. In an alternate embodiment, computer-controlled table movement is utilized and synchronized with the x-ray exposures such that a circle-plus-a straight line cone-beam geometry is utilized in order to optimize computational efficiency.

In its method aspects, the present invention is carried out by first injecting into the vein of patient a contrast fluid using an injector. Then, the portion of interest of the patient's body is scanned using the volume tomographic digital angiography system described herein. The projection data thus obtained is then preweighted and the partial derivatives of the preweighted projection data are calculated. The remaining steps described in conjunction with constructing an image from a volume CT or SPECT scanner discussed above are then utilized in order to generate the 3-D vascular images of interest for diagnostic and therapeutic uses.

With these and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

The following description of the theoretical underpinnings of the present invention is provided for background purposes.

As described above, this invention is directed to a method of and an apparatus for cone-beam tomography, which allows the processing of projection data which will be described herein to provide an artifacts-free reconstruction of a 3-D image.

Figure 1:
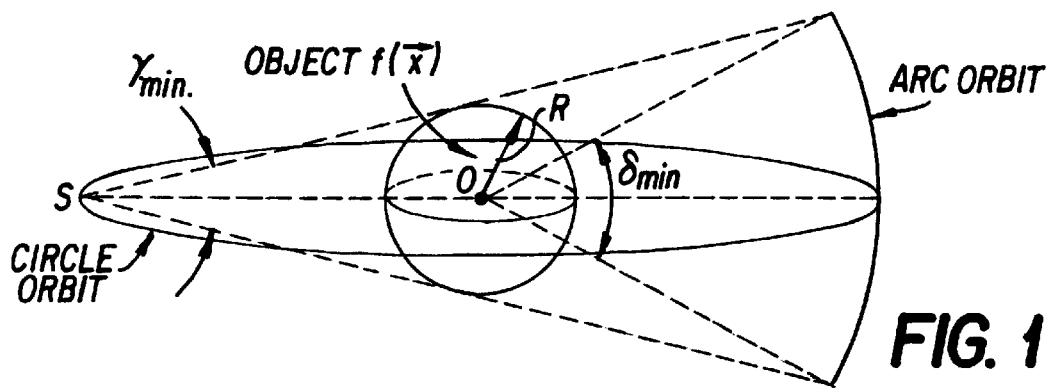
FIG. 1 is a drawing showing the geometry of the circle-plus-arc orbit utilized by the present invention.

In cone-beam tomography, the data sufficient condition must be fulfilled in order to obtain exact 3-D reconstructions. Tuy showed that the sufficient data condition requires that each plane passing through an object intersect the orbit of the focal point. In fact, dual orthogonal circles, orthogonal circle-and-line, and a helical orbit all satisfy Tuy's data sufficient condition for exact 3-D reconstructions. However, a single circular orbit does not, because planes parallel to the circular orbit do not contain any focal points on the orbit. In the present invention, a combination of a circular orbit and a small arc orbit is used. As shown in FIG. 1, the plane of the arc orbit is perpendicular to the circular orbit, and the two orbits intersect at the center of the arc. It is assumed that the two orbits are concentric at point O, and therefore have the same radius D (being concentric is assumed for the simplicity of mathematical derivation). The introduction of the arc orbit provides focal points for the planes which will not intersect the circular orbit. It is also assumed that the object function $f(\vec{x})$ has a finite boundary.

One extreme situation to the circle-plus-arc orbit is that the arc extends to a whole circle, therefore constructing two orthogonal circles. In that case, the radius R of the sphere that constrains the object function $f(\vec{x})$ has to satisfy the inequality:

$$D \geq \sqrt{2}\, R. \qquad (1)$$

As shown in FIG. 1, the cone-beam originating from point S should fully cover the object, i.e., $$\gamma_{min} \geq 2\sin^{-1}\left(\frac{R}{D}\right), \qquad (2)$$

where D is the radius of the circular orbit and $\gamma_{min}$ is the minimum required cone-angle.

In order to satisfy Tuy's data sufficient condition theorem, the arc orbit should supply focal points to planes which will not intersect the circular orbit. The outer-most one of those planes is tangential to both the circular orbit and the sphere of radius R which constrains the object and is perpendicular to the arc orbit plane. If the minimum arc spanning angle is represented as $\delta_{min}$, then from the geometry shown in FIG. 1, it follows that the inequality below should be satisfied:

$$\delta_{min} \geq 2\gamma_{min} \geq 4\sin^{-1}\left(\frac{R}{D}\right). \qquad (3)$$

The inequalities 2 and 3 guarantee that any plane that intersects the object will also intersect either the circular orbit or the arc orbit, therefore providing the data sufficient condition. Thus, the minimum spanning angle of the arc orbit should be no less than two times the minimum cone-angle.

The cone-beam projections and the 3-D Radon transform of an object will now be expressed in terms of the coordinate systems defined in this application. The cone-beam geometry is shown and defined in FIG. 2.

Figure 2:
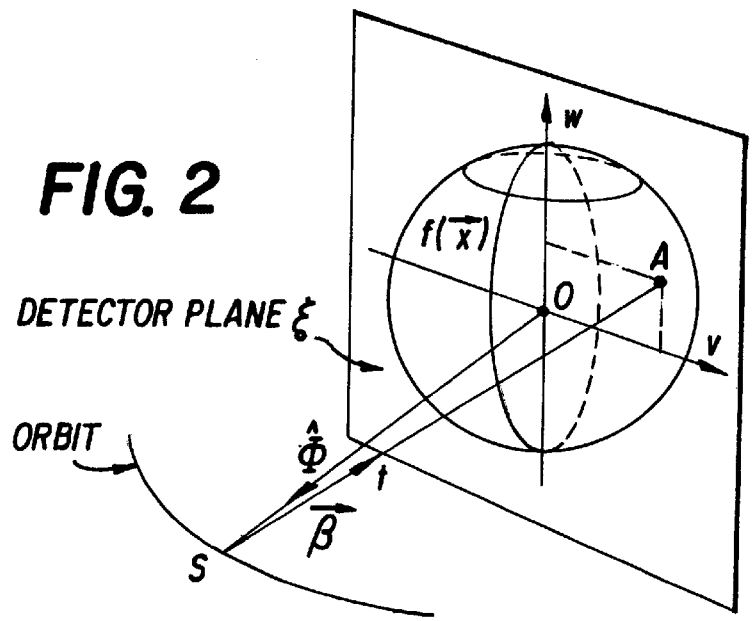
FIG. 2 is a drawing of the cone-beam geometry as used in connection with the present invention.

In the 3-D spatial space shown in FIG. 2, the point O is the origin of the coordinate system and $\vec{OS}=\vec{\Phi}$ is the position vector of the cone-beam focal point S. For purposes of the discussion herein, it will simplify mathematical derivation if the detector plane $\xi$ is defined in such a way that $\xi$ is perpendicular to the vector $\vec{OS}$ and always contains the point O. That convention will be used throughout this specification. Also, point A is any point in the detector plane and $\vec{\beta}$ is the unit directional vector of $\vec{SA}$.

In FIG. 2, a local detector Cartesian coordinate system uvw—O is also defined. The u-axis is coincident with the vector $\vec{OS}$ and the v-axis and w-axis are in the detector plane $\xi$ ($\vec{\Phi}$). Those local coordinates are discussed later herein in connection with the formula developed by Grangeat.

Cone-beam projections are generally defined as line integrals. If the object is characterized by some function $f(\vec{x})$, $\vec{x} \in R^3$, the cone-beam projection g of that object can be expressed as:

$$g(\vec{\Phi}, \hat{\beta}) = \int_{-\infty}^{+\infty} f(\vec{\Phi} + t\vec{\beta}) dt, \quad (4)$$

where $\hat{\beta}$ is also called the directional vector along the ray of the line integral.

Figure 3:
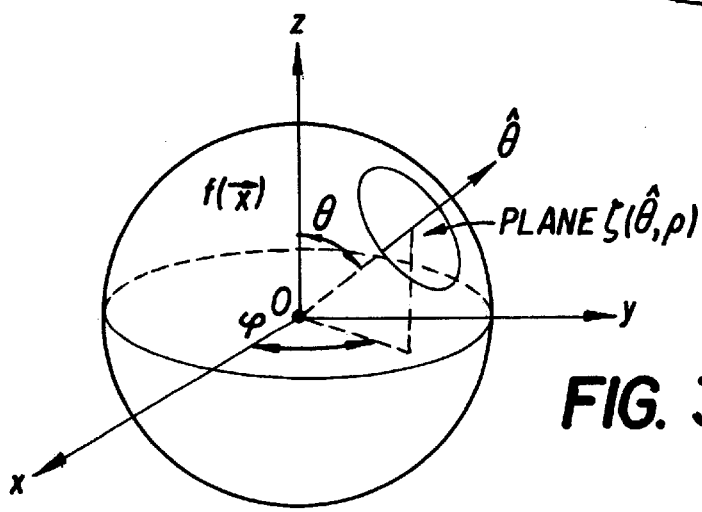
FIG. 3 is a drawing of the Radon transform geometry as used in connection with the present invention.

The Radon transform of a 3-D object is defined as plane integrals. Thus, the radon transform are integrals of the object function $f(\vec{x})$ in the planes $\zeta(\hat{\theta},\rho)$, where $\hat{\theta}$ is the normal vector of the plane $\zeta$ and $\rho$ is the distance from the plane $\zeta$ to the origin of the coordinates, point O. In the 3-D Cartesian space as shown in FIG. 3, any plane $\zeta$ can be uniquely defined by a unit vector $\hat{\theta}$ and a scalar $\rho$. Thus, $$\hat{\theta} = (\sin\theta\cos\phi, \sin\theta\sin\phi, \cos\theta), \quad (5)$$

is the normal vector to the plane $\zeta(\hat{\theta},\rho)$ and $\rho$ is the distance from that plane to the origin O of the coordinate system, $\theta \in [0, \pi)$, $\phi \in [0, \pi)$ and $\rho \in (-\infty, +\infty)$. The 3-D Radon transform R of an object $f(\vec{x})$ is defined as plane integrals:

$$R(\hat{\theta}, \rho) = \int\int\int_{-\infty}^{+\infty} f(\vec{x})\delta(\vec{x}\cdot\hat{\theta} - \rho) d\vec{x} \quad (6)$$

where the $\delta$ function constrains the 3-D integration in the plane $\zeta(\hat{\theta},\rho)$. The object function $f(\vec{x})$ can be exactly reconstructed by using the inverse 3-D Radon transform:

$$f(\vec{x}) = -\frac{1}{4\pi^2}\int_0^\pi d\varphi \int_0^\pi d\theta \sin\theta \left[\frac{\partial^2}{\partial\rho^2} R(\hat{\theta}, \rho)\right]_{\rho = \vec{x}\cdot\hat{\theta}}, \quad (7)$$

if $R(\vec{\theta},\rho)$ is known for every $(\vec{\theta}, \rho)$ on set M:

$$M \stackrel{\Delta}{=} \{(\hat{\theta}, \rho) \mid \theta \in [0, \pi), \varphi \in [0, \pi), \rho \in (-\infty, +\infty)\}.$$

Thus, in cone-beam tomography, the 3-D reconstruction of the object function $f(\vec{x})$ from its cone-beam projection data can be accomplished if the relationship is established between those projections and the object's 3-D Radon transform R.

P. Grangeat, in his work entitled "Mathematical framework of cone-beam 3-D reconstruction via the first derivative of the radon transform," *Mathematical Methods in Tomography*, G. T. Herman, A. K. Lous, F. Natterer, Eds., Lecture Notes in mathematics, Springer Verlag, 1990, developed an exact formula in establishing the relationship between the cone-beam projections $g(\vec{\Phi}, \hat{\beta})$ of the object function $f(\vec{x})$ and the first derivative of its 3-D Radon transform $R(\hat{\theta},\rho)$. That formula is introduced here based on the coordinate systems defined in this specification.

Figure 4:
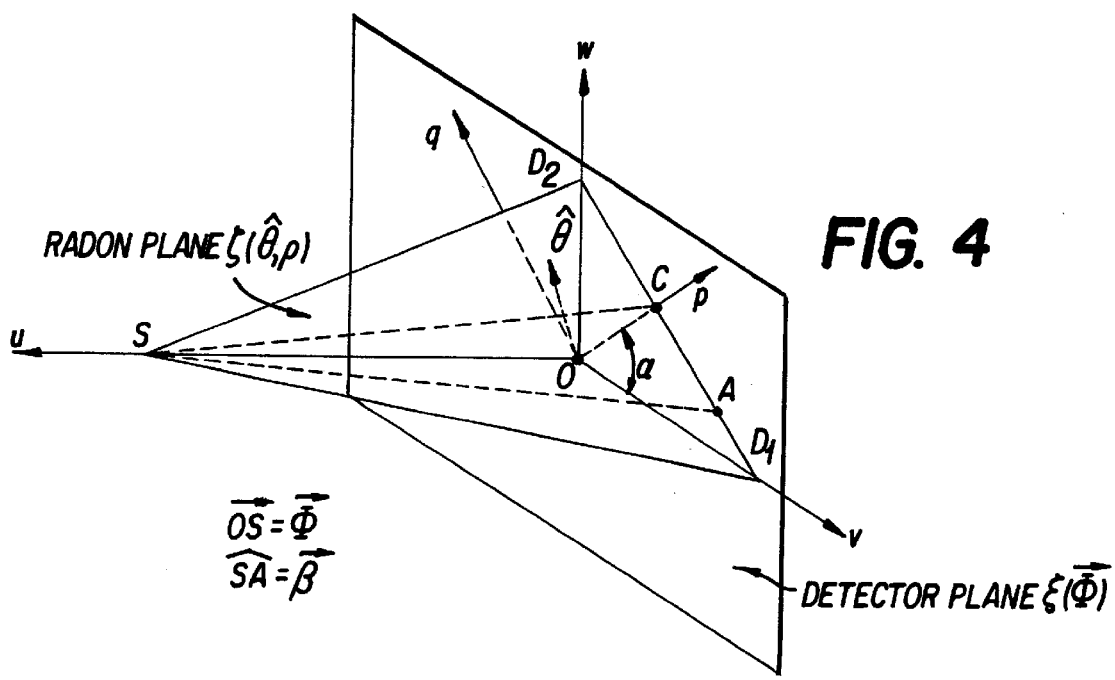
FIG. 4 is a drawing the cone-beam geometry showing the intersection of a Radon plane.

Referring now to FIG. 4, the detector plane $\zeta$ is defined in such a way that $\zeta$ is perpendicular to the vector $\vec{OS}=(\vec{\Phi})$ and always contains the point O, which is the origin of the coordinate system shown in FIGS. 2 and 4. Therefore, the plane $\zeta$ is uniquely defined by the vector $\vec{\Phi}$, i.e., $\zeta=\zeta(\vec{\Phi})$.

The orientations of the v-axis and the w-axis of the local detector coordinate system uvw—O are arbitrary but normally they take the physical orientations of the detector arrays. The Radon plane $\zeta(\vec{\theta},\rho)$, where the plane integral takes place, goes through the focal point S and intersects the detector plane $\zeta(\vec{\Phi})$ at line $D_1D_2$.

As shown in FIG. 4, another local Cartesian coordinate system upq-O is defined with the rotation of the v-axis and the w-axis about the u-axis by an angle $\alpha$, where $\alpha \in$ $$\left[-\frac{\pi}{2}, +\frac{\pi}{2}\right).$$

The p-axis should be perpendicular to the line $D_1D_2$ and their intersection point is C. Point A can be located anywhere on the line $D_1D_2$ and is assigned the coordinate (0, p, q) in the upq—O coordinate system. Therefore, the projection of the object function $f(\vec{x})$ along the line SA can be expressed in the local upq-O coordinates as:

$$g_{upq\text{-}O}(\vec{\Phi}, p, q) = \int_{-\infty}^{+\infty} f\left(\vec{\Phi} + \frac{\vec{SA}}{|\vec{SA}|}t\right) dt. \quad (8)$$

Having defined the cone-beam geometry and 3-D Radon plane, Grangeat's formula can be expressed as:

$$\frac{\partial}{\partial\rho} R(\hat{\theta}, \rho) = \frac{|\vec{SC}|^2}{|\vec{SO}|^2} \frac{\partial}{\partial p} \int_{-\infty}^{+\infty} \frac{|\vec{SO}|}{|\vec{SA}|} g_{upq\text{-}O}(\vec{\Phi}, p, q) dq. \quad (9)$$

Both $\vec{\Phi}$ and p in Equation 9 are functions of $\vec{\theta}$ and $\rho$, and the rebinning process is necessary to transform $\vec{\Phi}$ and p to the 3-D Radon space.

Rebinning to the Radon Domain (1) Preweighting of the Cone-beam Projections

According to Equation 9, a preweighting of the cone-beam projections should be performed prior to the rebinning process. The direct calculation of the preweighting can be achieved by utilizing the local uvw-O coordinate system, which is detector array oriented.

(2) Integration and Partial Derivative

As shown in Appendix A, the relationship between the first derivative and the preweighted cone-beam projections is given by:

$$\frac{\partial}{\partial\rho} R(\hat{\theta}, \rho) = \frac{|\vec{SC}|^2}{|\vec{SO}|^2} \int_{-\infty}^{+\infty} \left[\cos\alpha \frac{\partial}{\partial v} G_{uvw\text{-}O}(\vec{\Phi}, v, w) + \sin\alpha \frac{\partial}{\partial w} G_{uvw\text{-}O}(\vec{\Phi}, v, w)\right] dq. \quad (10)$$

Since the partial derivatives $$\frac{\partial}{\partial v} G_{uvw\text{-}O}(\vec{\Phi}, v, w) \text{ and } \frac{\partial}{\partial w} G_{uvw\text{-}O}(\vec{\Phi}, v, w)$$

on the right-hand side of Equation 10 need to be calculated only once, the computational complexity is significantly reduced. In implementing the present invention, these partial derivatives are calculated by convoluting (using FFT) a 1-D ramp filter with $G_{uvw\text{-}O}(\vec{\Phi},v,w)$ for a fixed $(\vec{\Phi}, w)$ and a fixed $(\vec{\Phi}, v)$, respectively. To get the best results, the ramp filter is first implemented in the spatial domain to avoid any dc-shift and then multiplied with a Hamming window in the frequency domain to reduce the reconstruction noise. A line integral algorithm based on a linear interpolation between pixels is applied to Equation 10 for the integration calculations, as shown in the article by Y. Weng, et al. entitled "A Reconstruction Algorithm for Helical Cone-Beam SPECT," *IEEE Transactions in Nuclear Science*, Vol. 40, No. 4, pp. 1092–1101, August 1993.

(3) The Rebinning Process

The rebinning process maps the results on the right-hand side of Equation IO to the Radon space, i.e., from uvw-O coordinates to ($\vec{\Phi}$,p) coordinates. A unit vector $\hat{\theta}$ can be expressed by two scalar parameters $\theta$ and $\phi$, as in Equation 5; thus the Radon space can be represented by the three scalars $\theta$, $\phi$ and p. In this specification, $\theta$, $\phi$ and p are all linearly quantized into 256 levels in the domain $$M \triangleq \{(\vec{\theta},\rho) | \theta \in [0, \pi), \phi \in [0, \pi), \rho \in (-R, +R)\}.$$

Each point ($\theta$, $\phi$, p) in the Radon domain is then mapped back to the projection domain ($\vec{\Phi}$,v,w) and interpolation is accomplished in the projection domain. For that purpose, a new set of rebinning equations have been derived for the circle and arc orbit separately. In the above-cited article, Weng et al. have suggested one method in which the parameters p, $\alpha$ and $\beta$ are discrete and the interpolation is accomplished in the 3-D Radon space. While such a process is appropriate to a helical orbit and can reduce the computational load, it is not suitable to the circle-plus-arc orbit geometry of the present invention because the finite quantization levels of p, $\alpha$ and $\beta$ will introduce large discontinuities in the Radon domain and therefore severe artifacts will be shown in the reconstructed images.

(a) Rebinning from the Circular Orbit

Figure 5:
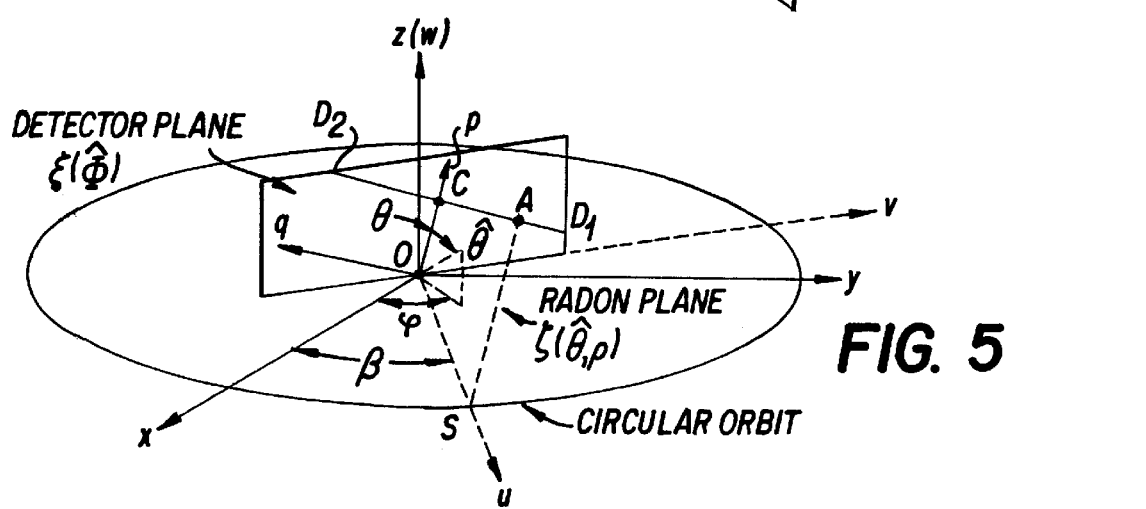
FIG. 5 is a diagram showing projection data taken from the circular orbit.

As shown in FIG. 5, any Radon plane that intersects the circular orbit has two intersection points, except when the Radon plane is tangential to the circular orbit. Either intersection point represents a corresponding focal point position. In order to improve the quality of the reconstructed images, both projections from the two focal points are used. First, the two intersection points are named $B_1$ and $B_2$, respectively, and the position arrangement for $B_1 \to B_2 \to O$ is counter-clockwise. Second, the angle between $O\vec{B}_1$ and the x-axis is $\beta_1$ and that between $O\vec{B}_1$ and the x-axis is $\beta_2$. Then, for a given point ($\theta$, $\phi$, p) in the Radon space, $\beta_1$ and $\beta_2$ can be calculated directly from the coordinates of point $B_1$ and point $B_2$, respectively. As derived in Appendix B, p and $\alpha$ can be solved exactly for a given $\theta$, $\phi$ and p: for $\beta_1$:

$$p = \frac{D|\rho|}{\sqrt{D^2 - \rho^2}}, \quad (11a)$$

$$\alpha = \begin{cases} \sin^{-1}\left(\frac{D\cos\theta}{\sqrt{D^2 - \rho^2}}\right) & \text{for } \rho \geq 0, \\ -\sin^{-1}\left(\frac{D\cos\theta}{\sqrt{D^2 - \rho^2}}\right) & \text{for } \rho < 0, \end{cases} \quad (11b)$$

and for $\beta_2$:

$$p = -\frac{D|\rho|}{\sqrt{D^2 - \rho^2}}, \quad (12a)$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0, \end{cases} \quad (12b)$$

Consequently, if $\theta$, $\phi$, $\rho$ and $\beta$ are discrete parameters, for a given ($\theta$, $\phi$, $\rho$) in the Radon space, only a 1-D interpolation relative to $\beta$ needs to be calculated for the rebinning process, which greatly reduces the interpolation errors. From the above solutions, to find the region where the projection data from the circular orbit can contribute to the Radon space:

$$|\cos\theta| = \frac{D\sin\alpha}{\left|\sqrt{D^2 + p^2}\right|} \leq \frac{D}{\sqrt{D^2 + p^2}} = \frac{\sqrt{D^2 + \rho^2}}{D} \text{ for } \alpha \in \left[-\frac{\pi}{2}, \frac{\pi}{2}\right), \quad (13)$$

i.e., $$\theta_c \leq \theta \leq \pi - \theta_c, \text{ where } \theta_c = \cos^{-1}\left(\frac{\sqrt{D^2 + \rho^2}}{D}\right),$$

which is the mathematical proof why a single circular orbit does not satisfy Tuy's data sufficient condition.

(b) Rebinning from the Arc Orbit

From Equation 13, it can be seen that the region of the Radon space that the projection data can contribute to the arc orbit is:

$$\theta \leq \theta < \theta_c \text{ or } \theta_c < \theta < \pi, \text{ where } \theta_c = \cos^{-1}\left(\frac{\sqrt{D^2 + \rho^2}}{D}\right). \quad (14)$$

Figure 6:
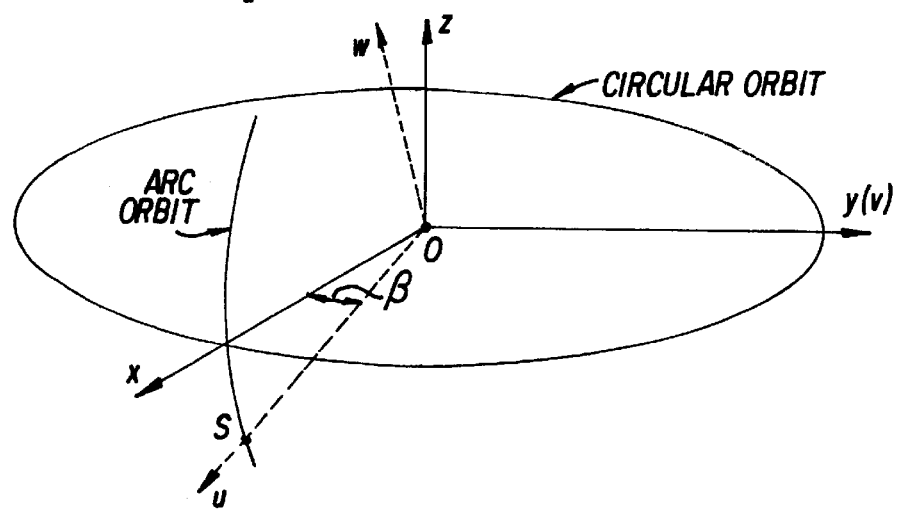
FIG. 6 is a diagram showing projection data taken from the arc orbit.

Referring to FIG. 6, it is seen that the arc orbit comes with the rotation of the focal point S about the y-axis by an angle $\beta$ and $\vec{OS}$ is defined as the u-axis. As derived in Appendix C, p and $\alpha$ can be solved exactly for a given ($\theta$, $\phi$, $\rho$):

$$p = \frac{D\rho}{\sqrt{D^2 - \rho^2}}, \quad (15a)$$

$$\alpha = \sin^{-1}\left(\frac{\frac{D}{\sqrt{D^2 + \rho^2}}\sin\theta\cos\varphi - \frac{\rho}{\sqrt{D^2 - \rho^2}}\cos\beta}{\sin\beta}\right). \quad (15b)$$

Once again, only the 1-D interpolation with regard to $\beta$ needs to be calculated for the discrete values of the parameters $\theta$, $\phi$, $\rho$ and $\beta$.

(4) Reconstruction of the Object Function

After the first derivative of the Radon transform $$\frac{\partial}{\partial \rho} R(\hat{\theta}, \rho)$$

is obtained from the rebinning process, the calculation of the second derivative can be accomplished by convoluting $$\frac{\partial}{\partial \rho} R(\hat{\theta}, \rho)$$

with a 1-D ramp filter. In order to obtain the best results, the ramp filter is first implemented in the spatial domain to avoid a dc-shift and then multiplied with a Hamming window in the frequency domain in order to reduce the reconstruction noise. The object function can then be reconstructed by using backprojection as indicated in Equation 7.

Figure 8:
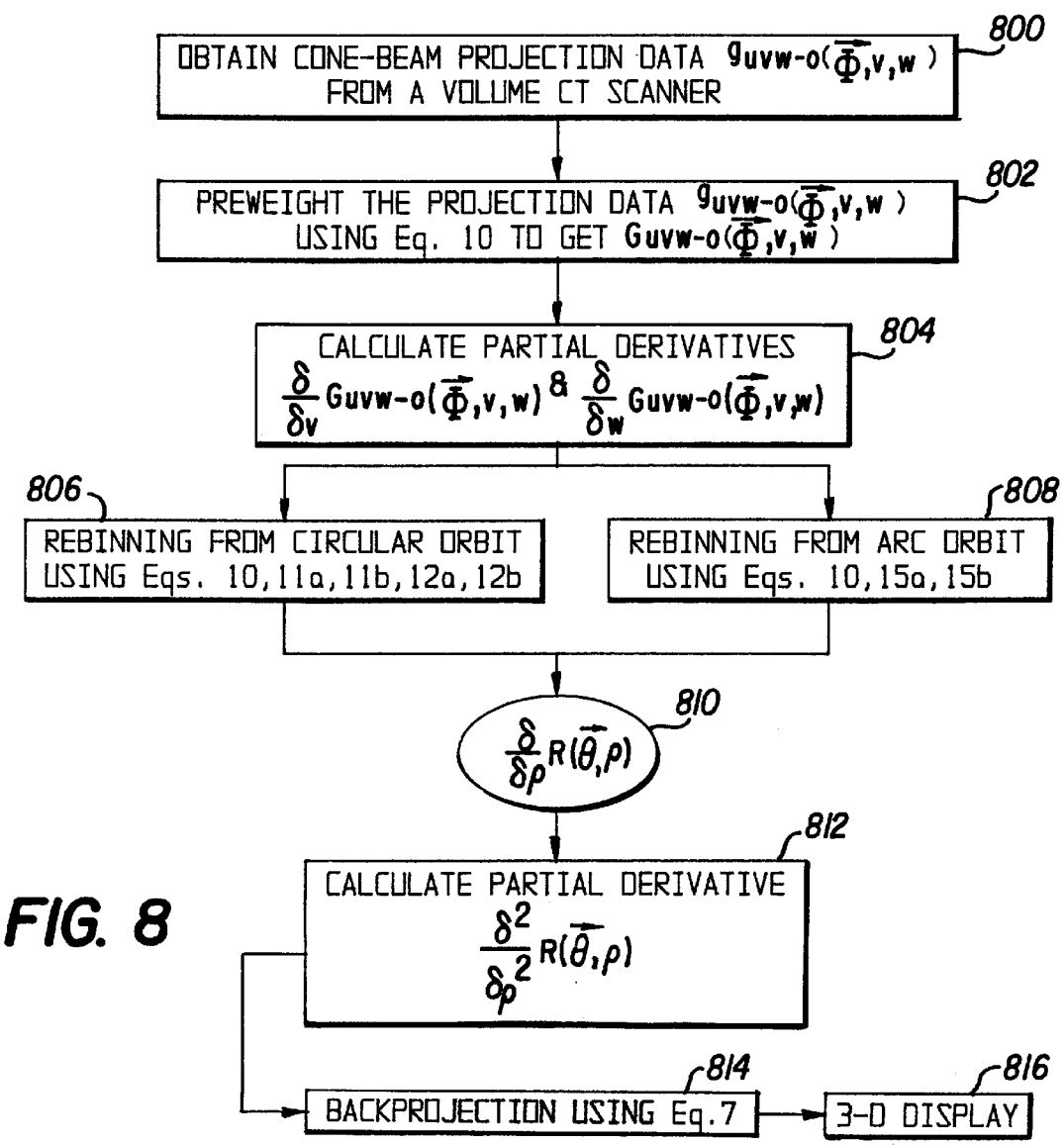
FIG. 8 is a diagram of a flow chart showing the steps performed in converting the projection data from a volume CT scanning apparatus to the cone-beam reconstruction matrix and a desired 3-D tomography display.

Referring now to FIG. 8, which is a diagram of a flow chart showing the steps performed in converting the projection data from a CT scanning apparatus to the desired 3-D display, in the first step 800, the cone-beam projection data is obtained from a volume CT scanner. Then, the projection data $g_{uvw-o}(\vec{\Phi}, v, w)$ is preweighted using Equation 10 in order to obtain the preweighted projection data $G_{uvw-o}(\vec{\Phi}, v, w)$ in Step 802. Then, at Step 804, the partial derivatives $$\frac{\partial}{\partial_v} G_{uvw-o}(\vec{\Phi}, v, w) \text{ and } \frac{\partial}{\partial_w} G_{uvw-o}(\vec{\Phi}, v, w)$$

are calculated. In Step 806, the results from the partial derivatives obtained in Step 804 are used to rebin the data from the circular orbit, using Equations 10, 11a, 11b, 12a and 12b. At Step 808, the partial derivatives calculated in Step 804 are used to rebin data from the arc orbit, using Equations 10, 15a and 15b.

In Step 810, the results from the rebinning from the circular and arc orbits are utilized to obtain the partial derivatives $$\frac{\partial}{\partial_p} R(\hat{\theta}, \rho).$$

Next, the partial second derivatived $$\frac{\partial^2}{\partial_p^2} R(\hat{\theta}, \rho)$$

is calculated at Step 812. Then, at Step 814, the back projection data is calculated, using Equation 7. Finally, at Step 816, the 3-D image is displayed.

Figure 9:
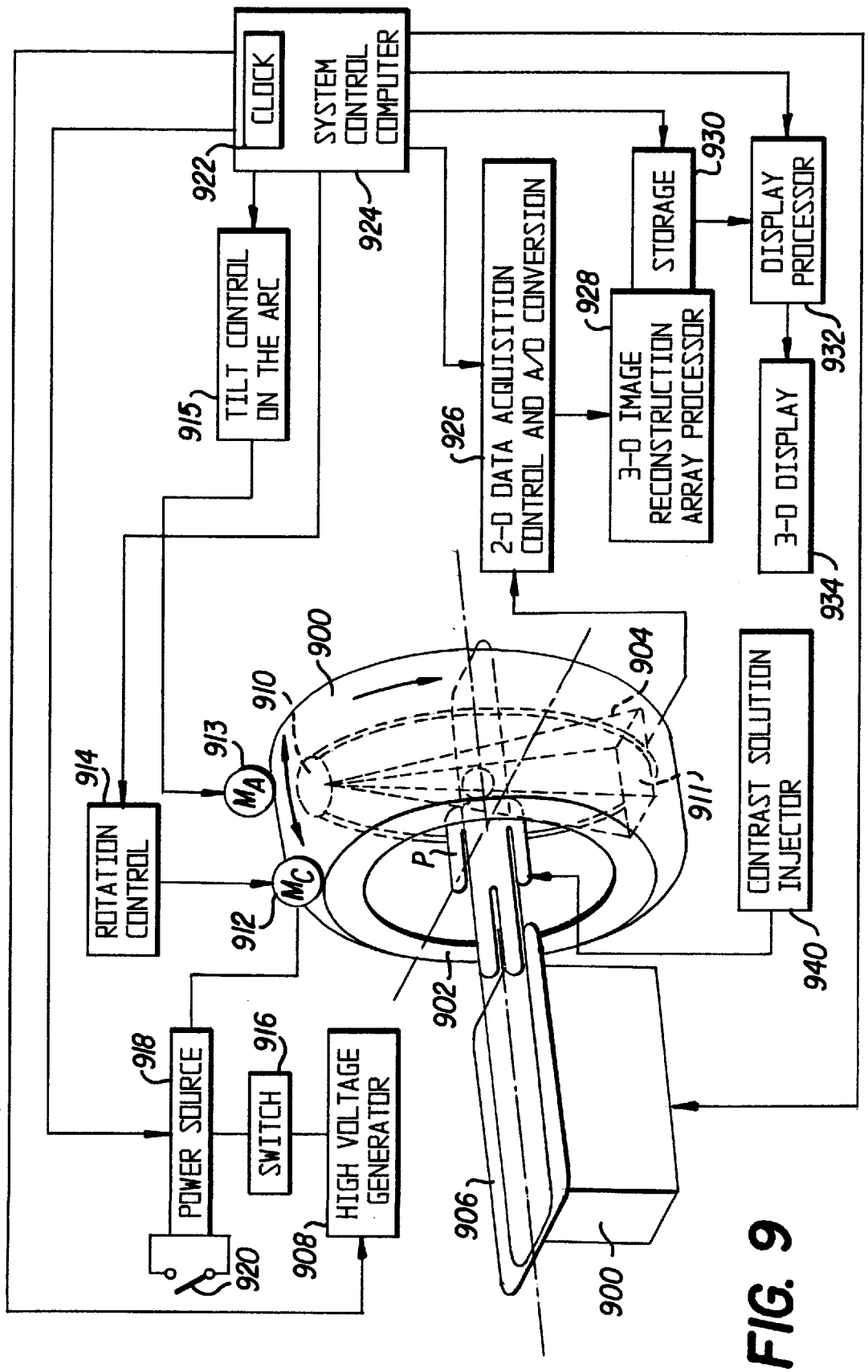
FIG. 9 is a schematic block diagram showing the use of the inventive intravenous volume tomographic angiography imaging system.

In a standard CT, a 3-D reconstruction is obtained by stacking a series of slices. In a volume CT, a direct reconstruction of an object can be obtained. Referring now to FIG. 9, it is shown how the cone-beam tomography system 900 of the present invention can be used to obtain a direct 3-D reconstruction of an object. It should be understood that the volume CT scanning apparatus 900 is illustrated in a simplified block diagram form. The invention may preferably be employed in conjunction with such a volume CT scanning apparatus to generate a 3-D reconstruction matrix of the object. Based on the 3-D reconstruction matrix, the desired three dimensional display can be obtained.

A volume CT scanning apparatus examines a body P which rests on a motorized table 906 using a cone shaped radiation beam 904 which traverses a set of paths across the body. As shown in FIG. 9, an x-ray source 910 and a 2-D detector 911 are mounted on a gantry frame 902 that rotates around the body P being examined. The operating voltage for the x-ray source is obtained from a conventional high-voltage generator 908 in such a manner that the x-ray source 910 produces the desired cone-shaped beam of radiation when the high-voltage is applied to it. The high-voltage generator 908 is energized by means of a power source 918, through a switch 916.

A first motor 912 is also powered by the power source 918 such that it drives the gantry frame 902 in its orbit about the body, for example, in a clockwise direction as shown by the arrows adjacent to the frame. The power source 918 is turned on by means of the switch 920 or other conventional control devices, in order to initiate a measurement sequence. A speed control circuit 914 is used to control the speed of rotation of the gantry frame 902 and to provide an output control signal which indicates when the speed of the motor 912 is at the desired level for taking measurements. The output from the rotational control 914 may also be utilized to operate the switch 916 such that the high-voltage generator 908 is only turned on when the gantry frame 902 is driven at the desired speed for making measurements.

In order to obtain the arc measurements as previously discussed, a tilt control 915 is utilized to cause the gantry frame 902 to tilt by a relatively small angle of ±15° to ±30°, by means of the gantry frame tilt motor 913. That tilting allows the acquisition of arc projection data on the perpendicular arc. Such geometry results in a complete set of data for an object with a 25–40 cm diameter corresponding to a 37–60 cm field at the detectors 911 with a magnification of 1.5. Although the tilting of the gantry 902 is generally available in a standard CT gantry, to acquire arc projections, the minimal modification of a standard CT gantry has to be made such that the tilting of the gantry, x-ray exposure timing and the projection acquisition are synchronized by the system control computer 924 as shown in FIG. 9. The system control computer 924 also functions to control the movement of the motorized examination table 906 in relation to the gantry frame 902, for utilizing a circle-plus-line geometry as described later herein.

In addition to the method described above to acquire circle and arc projections, alternatively, the circle-plus-arc geometry can be implemented in one of the following two ways. In the first and preferred of the three methods, the gantry 902 is tilted to a small angle (±15° to ±30°) and then the x-ray tube 910 and the 2-D detector 911 are rotated while the gantry 902 is tilted. A half set of arc projections will be acquired only when the x-ray tube 910 and the 2-D detector 911 are at the rotation angle of 0°. When the tilted angle becomes zero, the circle projections will be acquired at the preset rotation angle positions. When the circle projection acquisition is completed, the gantry 902 will be tilted toward −15° to −30°. Another half set of arc projections will be acquired only when the x-ray tube 910 and the 2-D detector 911 are at the rotation angle of 0°.

The second alternative method is to mechanically modify a standard CT gantry such that two short arc orbits are added to the gantry, and the x-ray tube 910 and the 2-D detector 911 can be moved on the arc to acquire the arc projections and on the circle to acquire the circle projections. One arc constitutes the orbit of the x-ray tube 910 and the other arc is the orbit of the 2-D detector 911. The two arc orbits are mounted 180° apart from each other. The x-ray tube 910 and the 2-D detector 911 are synchronously moved on the arc orbits to acquire arc projections. Then, the x-ray tube 910 and the 2-D detector 911 are rotated on the gantry to acquire circle projections.

Mounted on the gantry frame 902 opposite the x-ray source 910 is a 2-D detector 911 which has a dynamic range equal to or greater than 1000:1 and an image lag of less than 10%, for example a selenium thin film transistor (STFT) array or a silicon STFT array, in order to provide 2-D projections that correspond to an x-ray attenuation signal pattern. The x-ray source 910 and the 2-D detector 911 are mounted on the gantry frame 902 in such a manner that they both move synchronously.

The cone-shaped beam of radiation 904 generated by the x-ray source 910 is projected through the body or object under test. The 2-D detector cone measures the radiation transmitted along the set of beam paths across the cone.

Alternatively, a continuous series of two-dimensional detectors (not shown) can be fixedly mounted proximate to the gantry frame 902 and the x-ray source 910 is mounted to the gantry frame such that, upon rotation of the gantry frame, the cone-shaped radiation beam 904 is projected through the body P under test and sequentially received by each of the series of detectors.

A 2-D projection acquisition control and A/D conversion unit 926, under control of the scanning pulses sequentially obtained from the system control computer 924, which includes the clock 922, receives a sequence of outputs corresponding to different lines of the 2-D detector 911. Each line of the 2-D detector consists of many detection cells (at least>100). The output of each detector cell represents a line integral of attenuation values measurable along one of the respective beam paths. The cone-shaped beam 904 subtends a cone angle sufficient to include the entire region of interest of the body. Thus, a complete scan of the object can be made by merely orbiting the gantry frame 902 supporting the x-ray source 910 and the 2-D detector 911 around the body to acquire the 2-D projection signals at different angular positions.

The analog-to-digital conversion unit 926 serves to digitize the projection signals and to save them in the 3-D image reconstruction array processor 928 and storage device 930. The method employed by the 3-D image reconstruction array processor 928 is the invented algorithm described in this application. The 3-D image reconstruction array processor 928 serves to transform the digitized projection signals into x-ray attenuation data vectors. The x-ray attenuation data matrix corresponds to x-ray attenuation at spaced grid locations within the body trunk being examined. Each data element of the matrix represents an x-ray attenuation value and the location of the element corresponds to a respective 3-D grid location within the body.

In accordance with the principles of the invention discussed previously, a display processor 932 obtains the data stored as 3-D x-ray attenuation signal patterns in the memory storage 930, processes that data as previously described, for example, in connection with FIG. 8, and then the desired 3-D images are displayed on a 3-D display device 934.

The 3-D image reconstruction array processor 932 may, for example, be comprised of an ULTRA SPARC-1 model workstation, available from Sun Microsystems, Inc. of Mountain View, Calif. 94043.

The volume CT scanner system described above and shown in FIG. 9 can also be used to obtain clinically useful 3-D vascular images for enabling diagnostic and therapeutic decisions when used as an IV-VTDA system.

The IV-VTDA system of FIG. 9, when operated to perform IV-VTDA 3-D imaging, preferably uses a 2-D detector 911 such as a selenium or Silicon thin film transistor (TFT) plat panel detector, available from Sterling Diagnostic Imaging, Inc. of Newark, Del. 19714 or Varian Associates, Inc., of Palo Alto, Calif. 94304 (for example, model VIP-540X/ARM TFT). Preferably, such TFT detector is capable of acquiring projections at a rate of 30 or more frames/second, with each frame containing 512×512×12 or higher bits of data. Thus, using such a detector, a single volume scan of a selected object of interest can be completed within about 5.0–8.0 seconds. Therefore, IV-VTDA is relatively insensitive to motion artifacts.

Alternatively, the 2-D detector 911 may be formed by an image intensifier (II) coupled to a charge coupled device (CCD), such as a CCD camera. However, a flat panel detector as described above provides better contrast and spatial resolution, as well as better geometric accuracy, than an image intensifier based detector. In addition, if an II based detector, such as an II-CCD detector is utilized as the detector 911, then pincushion and "S" distortion algorithms need to be utilized to correct for the curvature of the input surface of the II (pincushion distortion) and for the earth's magnetic field (S distortion). Such algorithms are known in the art. For example, see X. Wang and R. Ning, "Accurate and Efficient Image Intensifier Distortion Correction Algorithm for Volume Tomographic Angiography," Proc. SPIE 1997; 3032:427–440.

Three different data acquisition geometries can alternatively be utilized with the IV-VDTA system of the present invention, depending on the cone beam angle. If the cone beam angle is less than 5 degrees, then a single circle cone beam data acquisition geometry using Feldkamp's reconstruction algorithm for 3-D image reconstructions of vascular structure can be used. If the cone beam angle is greater than 5 degrees, then the IV-VTDA system of the present invention should use either a circle-plus-arc or circle-plus-line cone beam data acquisition geometry in order to obtain a complete set of projection data for the exact 3-D reconstruction of the imaged vascular structures.

In order to obtain an exact 3-D reconstruction when using a circle-plus-arc cone beam data acquisition geometry, the algorithm discussed above in connection with volume CT scanning should be utilized. The circle-plus-line cone beam data acquisition geometry is another method which can be used to solve the problem of the incompleteness of projection data from the single circle cone beam geometry. That geometry corresponds to rotating the x-ray tube 910 and the 2-D detector 911 on the gantry 902 and then acquiring the line projections by moving the table 906. An appropriate algorithm for the circle-plus-line cone beam data acquisition geometry was developed by G. S. Zheng and G. T. Gullberg and is described in "A cone-beam tomography algorithm for orthogonal circle-and-line orbit," *Phys. Med. Biol.* 1992; 37:563–577, and has been applied by H. Hu, "A new cone beam reconstruction algorithm for the circle-and-line orbit," *Proceeding of* 1995 *Int'l Meeting on Fully* 3D *Image Reconstruction in Radiology and Nuclear Medicine*, pp. 303–310.

As will be obvious to those of ordinary skill in the art, the IV-VTDA system of the present invention can be used for performing whole body vascular imaging procedures. The IV-VTDA system of the present invention uses an intrinsically high object contrast associated with CT imaging. For example, even a 70:1 dilution of 350 mgI/ml contrast material within an artery provides more than 100 HUs of image contrast at 60 keV, the effective energy at which a standard CT scanner functions when the voltage of the x-ray tube is 100 kV.

Thus, the IV-VTDA system of the present invention is able to image a contrast having a concentration about three times more dilute than that usually achieved during a conventional IV-DSA study, while still obtaining acceptable image quality. Thus, using the IV-VTDA system of the present invention with a flat-panel detector, sufficient low contrast resolution is obtained to isolate the injected iodinated contrast signal in a 2 mm artery and spatial resolution to detect a 25% stenosis of a 2 mm artery in the human body is achieved. Since TFT detectors are capable of acquiring projections at a rate of 30 or more frames/seconds, each of which contains 512×512×12 or higher bits of data, a single volume scan can be completed within 5.0–12.0 seconds. Thus, IV-VTDA is relatively insensitive to motion artifacts and is superior to IA angiography. By using the IV-VTDA system of the present invention in place of IA, the arterial puncture and IA catheter risks and expense are eliminated.

The imaging protocols used with the IV-VTDA system of the present invention significantly improved the delineation, localization and visualization of non-cardiac vascular anatomy and disease. The IV-VTDA system of the present invention has five important advantages over current conventional digital angiography systems. First, the IV-VTDA system of the present invention provides true 3-D reconstructions that can be viewed at any angle or plane and that can be rotated around any axis. As is known to those of ordinary skill in the art, multiple views of the same vascular anatomy often convey more information than do only one or a few views. In addition, changing the viewing angle can make the difference between detecting and missing a significant lesion.

Second, the IV-VTDA system of the present invention allows for the direct measurement of the area of lumina stenosis which allows a more objective decision regarding whether or not the patient should undergo an invasive procedure or should be treated with medication. Presently, radiologists and surgeons can only estimate the area of stenosis based on one or several 2-D projection images. The improved accuracy of disease measurement obtainable with the IV-VTDA system of the present invention will also allow for a finer analysis in outcomes research for the evaluation of medical or surgical therapy. A 3-D data set is also more amenable to automated 3-D computerized lesion quantification techniques.

A third advantage of the IV-VTDA system of the present invention over conventional DSA systems is that the IV-VTDA system decreases the risk of embolization of atherosclerotic plaque by eliminating the catheterization which is necessary for IA angiography.

A fourth improvement is that the IV-VTDA system of the present invention provides a more objective evaluation of the results of a particular interventional procedure because VTDA allows the identical angle view to be computed at different times such as before and after intervention. That greatly facilitates the evaluation of the progression or correction of a narrowing. Using conventional angiography, however, a radiologist may not see a particular vessel post-procedure from the same angle as it was seen pre-procedure.

The fifth advantage of the IV-VTDA system of the present invention over conventional digital angiography is that the IV-VTDA system eliminates the need for angiographers to perform trial runs to identify the correct angle from which to view the lesion. Since only a single volume scanning and a single fast contrast injection are necessary for data acquisition using the IV-VTDA system of the present invention, the total x-ray exposure necessary as well as the procedure time is reduced compared to those necessary in conventional DSA. For example, for a typical VTDA scan, the total patient entrance exposure for a typical 288 exposures is 836 mR, which represents more than a factor of 50 reduction in total patient entrance exposures used in a routine DSA procedure. A typical DSA procedure uses about 100 exposures at an average of 400 mR per exposure.

The IV-VTDA system of the present invention operates as follows to obtain a 3-D reconstruction image of a vascular structure of interest. First, the patient P, who has already been placed on the table 906, is moved into place within the gantry 902. Then, a single peripheral or central IV contrast injection is made into the venous structure of interest. The injector 940 will then inject iodinated contrast solutions, for example, OMNIPAQUE 300, available from Winthrop Pharmaceuticals, New York, N.Y. 10016, preferably into one or both antecubital fossa (for peripheral injection) or superior vena cava (for central injection).

The volume CT scanning apparatus shown in FIG. 9 is then placed in its operational state and the patient is instructed to hold his or her breath. Then, using a cone beam x-ray source 910 and a 2-D detector 911, such as the Selenium or Silicon TFT flat panel detector discussed above, fast volume scanning of the vascular anatomy of interest is performed when the injected contrast solution, flowing from the injection site mentioned above, arrives at the image site, i.e., the vascular anatomy of interest (after more than about a 4 second time delay, counted from the beginning of the injection). Assuming that the circle-plus-arc acquisition geometry is utilized, a 3-D reconstruction matrix of the vascular structure under study is obtained as discussed above in connection with the description of the use of the volume CT scanner of FIG. 9. The arc measurements are obtained, as previously discussed, using the tilt control 915. The projection data obtained from the CT scanning apparatus is converted to the desired 3-D display using the steps 800–816 shown in FIG. 8. The injector 940 is available from E-Z-EM, Inc., Westbury, N.Y. 11590.

In the event that a circle-plus-line data acquisition geometry is utilized, then the table 906 is moved relative to the gantry 902 in a known manner in order to generate the straight line projection data. Then, utilizing the steps 800 through 816, in which certain of the equations would be modified in accordance with the circle-plus-straight line data acquisition geometry, the cone-beam projection data can be converted to the desired 3-D display.

3-D images can be reconstructed from both subtraction projections and nonsubtraction projections. Subtraction projections will be formed in the following way: two sets of projection images, each set equally spaced over 360 degrees, will be acquired. One set of projections will be acquired without injected iodine contrast solution as a mask projection and another set of projections will be acquired with injected iodine contrast solution. Then, the subtraction will be performed on the angularly paired and logarithmically transformed images to form a set of subtraction projections. Preferably, the mask projections will be acquired first, and then the projections after injecting iodine contrast solution will be acquired. Subtraction and nonsubtraction projections for vascular reconstruction have different advantages. Subtraction increases the efficiency of the reconstruction by reducing the number of required projections and improves image quality by reducing the impact of scatter and beam hardening problems. Nonsubtraction allows for a simpler and possibly faster data acquisition protocol with the reconstruction protraying both arteries and reference structures, making them useful as anatomical landmarks.

Using the IV-VTDA system of the present invention, efficient contrast and spatial resolution is provided in order to visualize all vascular vessels presently amenable to interventional techniques. In addition, the IV-VTDA system of the present invention covers a much larger segment of the human body in the direction orthogonal to the slices within a single scan (approximately 3–4 times larger) than a spiral CT can cover, and without sacrificing image quality.

Although only a preferred embodiment is specifically illustrated and described herein, it will be readily appreciated that many modifications and variations of the present invention are possible in light of the above teachings and within the purview of the appended claims without departing from the spirit and intended scope of the invention.

APPENDIX A

With the relationship between the upq-O and the uvw-O coordinate systems (See FIG. 4), $$\begin{pmatrix} u \\ v \\ w \end{pmatrix} = \begin{pmatrix} 1 & 0 & 0 \\ 0 & \cos\alpha & -\sin\alpha \\ 0 & \sin\alpha & \cos\alpha \end{pmatrix} \begin{pmatrix} u \\ p \\ q \end{pmatrix}, \quad (16)$$

and variable substituting, $$\frac{\partial}{\partial p} G_{upq-O}(\vec{\Phi}, p, q) = \frac{\partial v}{\partial p} \frac{\partial}{\partial v} G_{uvw-O}(\vec{\Phi}, v, w) + \quad (17)$$
$$\frac{\partial w}{\partial p} \frac{\partial}{\partial w} G_{uvw-O}(\vec{\Phi}, v, w)$$
$$= \cos\alpha \frac{\partial}{\partial v} G_{uvw-O}(\vec{\Phi}, v, w) + \sin\alpha \frac{\partial}{\partial w} G_{uvw-O}(\vec{\Phi}, v, w).$$

As is known in the prior art, great computational efficiency and accuracy can be obtained by swapping the integral with the derivative in Equation 9. With Equation 10 in mind, by putting Equation 17 into Equation 9 and swapping the integral with the derivative, $$\frac{\partial}{\partial \rho} R(\theta, \rho) = \frac{|\vec{SC}|^2}{|\vec{SO}|^2} \frac{\partial}{\partial p} \int_{-\infty}^{+\infty} \frac{|\vec{SO}|}{|\vec{SA}|} G_{upq-O}(\vec{\Phi}, p, q) dq \quad (18)$$
$$= \frac{|\vec{SC}|^2}{|\vec{SO}|^2} \frac{\partial}{\partial p} \int_{-\infty}^{+\infty} G_{upq-O}(\vec{\Phi}, p, q) dq$$
$$= \frac{|\vec{SC}|^2}{|\vec{SO}|^2} \int_{-\infty}^{+\infty} \left[ \frac{\partial}{\partial p} G_{upq-O}(\vec{\Phi}, p, q) \right] dq$$
$$= \frac{|\vec{SC}|^2}{|\vec{SO}|^2} \int_{-\infty}^{+\infty} \left[ \cos\alpha \frac{\partial}{\partial v} G_{uvw-O}(\vec{\Phi}, v, w) + \sin\alpha \frac{\partial}{\partial w} G_{uvw-O}(\vec{\Phi}, v, w) \right] dq.$$

Since the partial derivatives $$\frac{\partial}{\partial v} G_{uvw-O}(\vec{\Phi}, v, w) \text{ and } \frac{\partial}{\partial w} G_{uvw-O}(\vec{\Phi}, v, w)$$

on the right-hand side of Equation 18 need to be calculated only once, the computational complexity is significantly reduced.

APPENDIX B

To fill the Radon cube $(\theta, \phi, \rho)$ with the projection data from the circular orbit, the transformation function should be found between the local uvw-O coordinates and the absolute xyz-O coordinates (see FIG. 5). The circular orbit lies in the xy plane and the focal point S will be restrained on this orbit. The angle between the x-axis and the vector $\vec{OS}$ is defined as $\beta$ and the angle between the p-axis and the v-axis is $\alpha$. If the point C is represented by (0, p, 0) in the local upq-O coordinate system, the Radon plane which contains the line $D_1D_2$ and the point S can be described in the uvw-O coordinate system as:

$$up + vD\cos\alpha + wD\sin\alpha - Dp = 0. \quad (19)$$

Referring to FIG. 5, the transformation between the local uvw-O coordinates and absolute xyz-O coordinates can be expressed as:

$$\begin{pmatrix} u \\ v \\ w \end{pmatrix} = \begin{pmatrix} \cos\beta & \sin\beta & 0 \\ -\sin\beta & \cos\beta & 0 \\ 0 & 0 & 1 \end{pmatrix} \begin{pmatrix} x \\ y \\ z \end{pmatrix}. \quad (20)$$

Therefore, the Radon plane represented by Equation 19 can be rewritten in the absolute xyz-O coordinates in terms of the parameters $\alpha$, $\beta$ and p as:

$$x(-D\cos\alpha\sin\beta + p\cos\beta) + y(D\cos\alpha\cos\beta + p\sin\beta) + zD\sin\beta - Dp = 0 \quad (21)$$

Comparing Equation 21 with the other representation of this Radon plane in terms of $\theta$ and $\rho$:

$$x\sin\theta\cos\phi + y\sin\theta\sin\phi + z\cos\theta - \rho = 0, \quad (22)$$

it can be shown that:

$$\sin\theta\cos\varphi \sim \frac{-D\cos\alpha\sin\beta + p\cos\beta}{\sqrt{D^2 + p^2}}, \quad (23a)$$

$$\sin\theta\sin\varphi \sim \frac{D\cos\alpha\cos\beta + p\sin\beta}{\sqrt{D^2 + p^2}}, \quad (23b)$$

$$\sin\theta\sin\varphi \sim \frac{D\cos\alpha\cos\beta + p\sin\beta}{\sqrt{D^2 + p^2}}, \quad (23c)$$

$$\cos\theta \sim \frac{D\sin\alpha}{\sqrt{D^2 + p^2}}, \quad (23c)$$

$$\rho \sim \frac{Dp}{\sqrt{D^2 + p^2}}, \quad (23d)$$

The symbol "~" is used instead of "=" in Equations 23a–23d because there may be a factor +1 or −1 involved. Any Radon plane (Equation 21) that intersects the circular orbit ($x^2 + y^2 = D^2$) has two intersection points except when the Radon plane is tangential to the circular orbit. Either point represents its corresponding focal point position. In order to improve the quality of the reconstructed images, both projections from the two focal points are used. First, the two intersection points are named $B_1$ and $B_2$ respectively, and the position arrangement for $B_1 \to B_2 \to O$ is counterclockwise. Second, the angle between $\vec{OB}_1$ and the x-axis is $\beta_1$ and that between $\vec{OB}_2$ and the x-axis is $\beta_2$. Then, for a given point $(\theta, \phi, \rho)$ in the Radon space, $\beta_1$ and $\beta_2$ can be calculated directly from the coordinates of point $B_1$ and $B_2$, respectively. The solutions to Equations 23a–23d can also be expressed as: for $\beta_1$:

$$p = \frac{D|\rho|}{\sqrt{D^2 - \rho^2}} \quad (24a)$$

-continued $$\alpha = \begin{cases} \sqrt{D^2 - \rho^2} \\ -\sin^{-1}\left(\dfrac{D\cos\theta}{\sqrt{D^2 - \rho^2}}\right) \text{ for } \rho < 0. \end{cases} \quad (24b)$$

and for $\beta_2$:

$$p = -\dfrac{D|\rho|}{\sqrt{D^2 - \rho^2}}, \quad (24c)$$

$$\alpha = \begin{cases} -\sin^{-1}\left(\dfrac{D\cos\theta}{\sqrt{D^2 - \rho^2}}\right) \text{ for } \rho \geq 0, \\ \sin^{-1}\left(\dfrac{D\cos\theta}{\sqrt{D^2 - \rho^2}}\right) \text{ for } \rho < 0. \end{cases} \quad (24d)$$

Therefore, if $\theta$, $\phi$, $\rho$ and $\beta$ are discrete parameters, for a given ($\theta$, $\phi$, $\rho$) in the Radon space, only a 1-D interpolation relative to $\beta$ need be calculated, which greatly reduces the interpolation errors.

APPENDIX C

Figure 7:
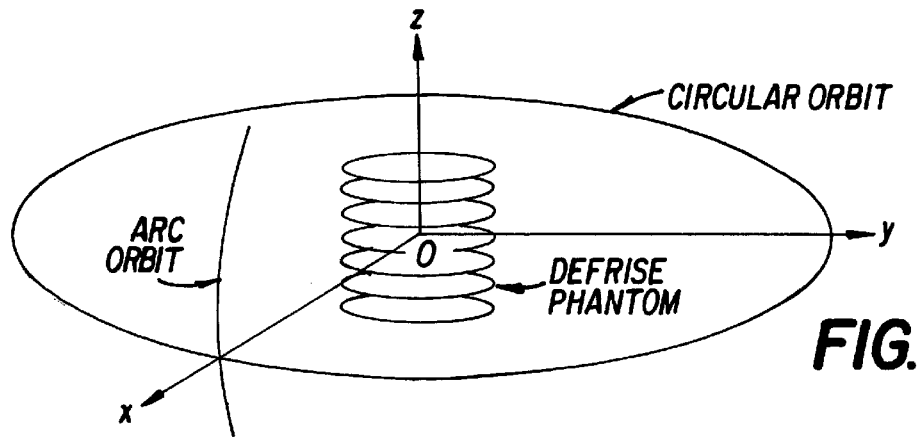
FIG. 7 is a drawing of the geometry of a Defrise Phantom and circle-plus-arc orbit.

Referring to FIG. 7, the arc orbit comes with the rotation of the focal point S about the y-axis by an angle $\beta$ and $\overrightarrow{OS}$ is defined as the u-axis. The transformation between the local uvw-O coordinate system and the absolute xyz-O coordinate system can be expressed as:

$$\begin{pmatrix} u \\ v \\ w \end{pmatrix} = \begin{pmatrix} \cos\beta & 0 & -\sin\beta \\ 0 & 1 & 0 \\ \sin\beta & 0 & \cos\beta \end{pmatrix} \begin{pmatrix} x \\ y \\ z \end{pmatrix}. \quad (25)$$

Again, the Radon plane represented by Equation 19 can be rewritten in the absolute xyz-O coordinates as:

$$x(D\sin\alpha\sin\beta + p\cos\beta) + yD\cos\alpha + y(D\sin\alpha\cos\beta - p\sin\beta) - Dp = 0 \quad (26)$$

Comparison with Equation 22, which is the representation of the Radon plane in terms of parameters $\hat{\theta}$ and $\rho$, yields the following results:

$$\sin\theta\cos\varphi = \dfrac{D\sin\alpha\sin\beta + p\cos\beta}{\sqrt{D^2 + p^2}}, \quad (27a)$$

$$\sin\theta\sin\varphi = \dfrac{D\cos\alpha}{\sqrt{D^2 + p^2}}, \quad (27b)$$

$$\cos\theta = \dfrac{D\sin\alpha\cos\beta - p\sin\beta}{\sqrt{D^2 + p^2}}, \quad (27c)$$

$$\rho = \dfrac{Dp}{\sqrt{D^2 + p^2}}, \quad (27d)$$

Therefore, the solution to the above equations for a given ($\theta$, $\phi$, $\rho$) are:

$$p = \dfrac{D\rho}{\sqrt{D^2 - \rho^2}}, \quad (28a)$$

$$\alpha = \sin^{-1}\left(\dfrac{\dfrac{D}{\sqrt{D^2 + \rho^2}}\sin\theta\cos\varphi - \dfrac{\rho}{\sqrt{D^2 - \rho^2}}\cos\beta}{\sin\beta}\right). \quad (28b)$$

Once again, only a 1-D interpolation relative to $\beta$ needs to be calculated for the discrete values of parameters $\theta$, $\phi$, $\rho$ and $\beta$.

What is claimed is:

1. Apparatus for performing intravenous tomographic digital angiography of a region of a patient which has received a contrast solution, comprising:

a moveable support on which said patient is placed;

a gantry frame which rotates around said patient;

a cone-beam x-ray source and a two-dimensional detector mounted 180° apart from each other on said gantry frame for synchronous rotation with said gantry frame;

means for acquiring data signals from said two-dimensional detector and for generating three-dimensional angiography images from said acquired data; and means for controlling motion of at least one of said moveable support and said gantry frame to implement a data acquisition geometry comprising a circle and one of (i) at least one arc projection and (ii) at least one line projection.

2. The apparatus of claim 1, wherein:

said data signals comprise circular projection signals and arc projection signals;

said two-dimensional detector defines a detector plane and has a local detector coordinate system with an origin, a Radon plane intersecting the detector plane to define a line of intersection, the origin and the line of intersection being connected by a p axis which is perpendicular to the line of intersection; and the means for acquiring comprises means for rebinning said data signals according to the following equations, where D is a radius of the circle, ($\theta$, $\phi$, $\rho$) is a given point in Radon space, p is a perpendicular distance from the origin to the line of intersection measured along the p axis, $\alpha$ is an angular orientation of the p axis relative to the local detector coordinate system, $\beta$ is an angle of rotation of said scanner relative to a plane of said circular orbit, and $\beta_1$ and $\beta_2$ are two points of intersection of the Radon plane with the circle:

(a) for said circular projection signals:

(i) for $\beta_1$:

$$p = \dfrac{D|\rho|}{\sqrt{D^2 - \rho^2}},$$

$$\alpha = \begin{cases} \sin^{-1}\left(\dfrac{D\cos\theta}{\sqrt{D^2 - \rho^2}}\right) \text{ for } \rho \geq 0, \\ -\sin^{-1}\left(\dfrac{D\cos\theta}{\sqrt{D^2 - \rho^2}}\right) \text{ for } \rho < 0, \end{cases}$$

(ii) for $\beta_2$:

$$p = -\frac{D|\rho|}{\sqrt{D^2 - \rho^2}},$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0, \end{cases}$$

(b) for said arc projection signals:

$$p = \frac{D\rho}{\sqrt{D^2 - \rho^2}},$$

$$\alpha = \sin^{-1}\left(\frac{\frac{D}{\sqrt{D^2 - \rho^2}}\sin\theta\cos\varphi - \frac{\rho}{\sqrt{D^2 - \rho^2}}\cos\beta}{\sin\beta}\right).$$

3. The apparatus of claim 1, further including means for positioning said moveable support with respect to said gantry frame.

4. The apparatus of claim 1, wherein said apparatus is operated utilizing a circle-plus-line cone-beam data acquisition geometry to obtain a set of projection data.

5. The apparatus of claim 1, wherein said two-dimensional detector is an image intensifier CCD detector.

6. The apparatus of claim 1, in which said contrast solution is only injected intravenously into said patient.

7. The apparatus of claim 1, wherein said apparatus is operated utilizing a circle-plus-arc cone-beam data acquisition geometry to obtain a set of projection data.

8. Apparatus for performing intravenous tomographic digital angiography of a region of a patient which has received a contrast solution, comprising:
   a moveable support on which said patient is placed;
   a gantry frame which rotates around said patient;
   a cone-beam x-ray source and a two-dimensional detector mounted 180° apart from each other on said gantry frame for synchronous rotation with said gantry frame;
   means for acquiring data signals from said two-dimensional detector and for generating three-dimensional angiography images from said acquired data; and
   means for tilting said gantry frame at an angle away from a plane perpendicular to said moveable support.

9. Apparatus for performing intravenous tomographic digital angiography of a region of a patient which has received a contrast solution comprising:
   a moveable support on which said patient is placed;
   a gantry frame which rotates around said patient;
   a cone-beam x-ray source and a two-dimensional detector mounted 180° apart from each other on said gantry frame for synchronous rotation with said gantry frame; and
   means for acquiring data signals from said two-dimensional detector and for generating three-dimensional angiography images from said acquired data;
   wherein said two-dimensional detector comprises one of a selenium or silicon thin film transistor array or a flat panel detector or an image intensifier detector.

10. Apparatus for performing intravenous tomographic digital angiography of a region of a patient which has received a contrast solution, comprising:
    a moveable support on which said patient is placed;
    a gantry frame which rotates around said patient;
    a cone-beam x-ray source and a two-dimensional detector mounted 180° apart from each other on said gantry frame for synchronous rotation with said gantry frame; and
    means for acquiring data signals from said two-dimensional detector and for generating three-dimensional angiography images from said acquired data;
    wherein said three-dimensional angiography images are exact 3-D reconstructions of imaged vascular structures.

11. Apparatus for performing intravenous tomographic digital angiography of a region of a patient which has received a contrast solution, comprising:
    a moveable support on which said patient is placed;
    a gantry frame which rotates around said patient;
    a cone-beam x-ray source and a two-dimensional detector mounted 180° apart from each other on said gantry frame for synchronous rotation with said gantry frame; and
    means for acquiring data signals from said two-dimensional detector and for generating three-dimensional angiography images from said acquired data;
    wherein a volume scan of said contrast solution receiving region of said patient is completed in a maximum of 12.0 seconds.

12. Apparatus for performing intravenous tomographic digital angiography of a region of a patient which has received a contrast solution, comprising:
    a moveable support on which said patient is placed;
    a gantry frame which rotates around said patient;
    a cone-beam x-ray source and a two-dimensional detector mounted 180° apart from each other on said gantry frame for synchronous rotation with said gantry frame; and
    means for acquiring data signals from said two-dimensional detector and for generating three-dimensional angiography images from said acquired data;
    wherein said two-dimensional detector is capable of acquiring projections at a rate of at least 30 or more frames per second.

13. Apparatus for performing intravenous digital angiography of a vascular structure of interest of a patient using a contrast solution, comprising:
    a radiation cone-beam scanner which generates cone-beam projection signals of said vascular structure of interest containing said contrast solution, said radiation cone-beam scanner comprising control means for controlling said radiation cone-beam scanner to generate said cone-beam projection signals utilizing a data acquisition geometry which comprises a circle and one of (i) at least one arc projection and (ii) at least one line projection; and
    means for converting said cone-beam projection signals into three-dimensional reconstructions of said vascular structure being imaged.

14. The apparatus of claim 13, wherein said radiation cone-beam scanner generates cone-beam circular projection signals representative of a circular orbit around said vascular structure and cone-beam arc projection signals representative of an arc about said vascular structure.

15. The apparatus of claim 13, wherein said radiation cone-beam scanner generates cone-beam circular projection signals representative of a circular orbit around said vascular structure and cone-beam line projection signals representative of a line parallel to said vascular structure.

16. The apparatus of claim 13, wherein said radiation is x-rays.

17. The apparatus of claim 13, in which said contrast solution is only injected intravenously into said patient.

18. The apparatus of claim 14, wherein:
said radiation cone-beam scanner comprises a two-dimensional detector which defines a detector plane an has a local detector coordinate system with an origin, a Radon plane intersecting the detector plane to define a line of intersection, the origin and the line of intersection being connected by a p axis which is perpendicular to the line of intersection; and the means for converting comprises means for rebinning said cone-beam projection signals according to the following equations, where D is a radius of a circular orbit of the radiation cone-beam scanner, $(\theta, \phi, \rho)$ is a given point in Radon space, p is a perpendicular distance from the origin to the line of intersection measured along the p axis, $\alpha$ is an angular orientation of the p axis relative to the local detector coordinate system, $\beta$ is an angle of rotation of said scanner relative to a plane of said circular orbit, and $\beta_1$ and $\beta_2$ are two points of intersection of the Radon plane with the circular orbit:

(a) for said cone-beam circular projection signals:
(i) for $\beta_1$:

$$p = \frac{D|\rho|}{\sqrt{D^2 - \rho^2}},$$

$$\alpha = \begin{cases} \sin^{-1}\left(\frac{D\cos\theta}{\sqrt{D^2 - \rho^2}}\right) & \text{for } \rho \geq 0, \\ -\sin^{-1}\left(\frac{D\cos\theta}{\sqrt{D^2 - \rho^2}}\right) & \text{for } \rho < 0, \end{cases}$$

(ii) for $\beta_2$:

$$p = -\frac{D|\rho|}{\sqrt{D^2 - \rho^2}},$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0, \end{cases}$$

(b) for said cone-beam arc projection signals:

$$p = \frac{D\rho}{\sqrt{D^2 - \rho^2}},$$

-continued $$\alpha = \sin^{-1}\left(\frac{\frac{D}{\sqrt{D^2 - \rho^2}}\sin\theta\cos\varphi - \frac{\rho}{\sqrt{D^2 - \rho^2}}\cos\beta}{\sin\beta}\right).$$

19. Apparatus for performing intravenous digital angiography of a vascular structure of interest of a patient using a contrast solution, comprising:
a radiation cone-beam scanner which generates cone-beam projection signals of said vascular structure of interest containing said contrast solution; and
means for converting said cone-beam projection signals into three-dimensional reconstructions of said vascular structure being imaged;
wherein said radiation cone-beam scanner completes a scan of said vascular structure of interest containing said contrast solution in a maximum of 12.0 seconds.

20. A method for generating a digital angiographic image of a vascular structure of interest using an intravenous injection comprising the steps of:
intravenously injecting a contrast solution such that it reaches said vascular structure of interest;
scanning said vascular structure of interest with a radiation cone-beam scanner including a two-dimensional detector;
generating a three-dimensional reconstruction matrix of said vascular structure of interest using data signals generated by said two-dimensional detector; and
generating a three-dimensional image of said vascular structure of interest using said three-dimensional reconstruction matrix;
wherein said scanning step is accomplished using a volume CT scanning apparatus having a gantry frame which rotates around said vascular structure of interest in a plane perpendicular thereto and in which said gantry frame is further capable of being tilted at an angle away from said perpendicular plane.

21. A method for generating a digital angiographic image of a vascular structure of interest using an intravenous injection, comprising the steps of:
intravenously injecting a contrast solution such that it teaches said vascular structure of interest;
scanning said vascular structure of interest with a radiation cone-beam scanner including a two-dimensional detector, said step of scanning being performed with a data acquisition geometry comprising a circle and one of (i) at least one arc projection and (ii) at least one line projection;
generating a three-dimensional reconstruction matrix of said vascular structure of interest using data signals generated by said two-dimensional detector; and
generating a three-dimensional image of said vascular structure of interest using said three-dimensional reconstruction matrix.

22. The method of claim 21, wherein said radiation is x-rays.

23. The method of claim 21, wherein said contrast solution is only injected intravenously such that it reaches said vascular structure of interest.

24. A method for generating a digital angiographic image of a vascular structure of interest using an intravenous injection, comprising the steps of:
intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said two-dimensional detector acquires projections at a rate of at least 30 or frames per second.

25. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said scanning step is completed in a maximum of 12.0 seconds.

26. Apparatus for performing intravenous digital angiography of a vascular structure of interest of a patient using a contrast solution, comprising:

a radiation cone-beam scanner which generates cone-beam projection signals of said vascular structure of interest containing said contrast solution; and means for converting said cone-beam projection signals into three-dimensional reconstructions of said vascular structure being imaged;

wherein said radiation cone-beam scanner includes a two-dimensional detector comprised of one of a selenium or silicon thin film transistor array or a flat panel detector or an image intensifier detector.

27. The apparatus of claim 26, wherein said two-dimensional detector is capable of acquiring projections at a rate of at least 30 or more frames per second.

28. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said scanning step further includes rotating said gantry frame around said vascular structure of interest and tilting said gantry frame while said gantry frame is rotating.

29. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said two-dimensional detector comprises one of a selenium or silicon thin film transistor array or a flat panel detector or an image intensifier detector.

30. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector to acquire first and second sets of nonsubtraction two-dimensional projections, said step of scanning being performed with a data acquisition geometry comprising a circle and one of (i) at least one arc projection and (ii) at least one line projection;

generating a three-dimensional reconstruction matrix of said vascular structure of interest using data signals generated by said two-dimensional detector; and generating a three-dimensional image of said vascular structure of interest using said three-dimensional reconstruction matrix.

31. The method of claim 30, wherein said first and second sets of two-dimensional projections are used to form a set of subtraction projections.

32. The method of claim 30, wherein said first set of two-dimensional projections is acquired before injecting said contrast solution and said second set of two-dimensional projections is acquired after injecting said contrast solution.

33. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said step of intravenously injecting is performed at a vena cava near a right atrium.

34. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said step of intravenously injecting is performed through a peripheral vein.

35. The method of claim 34, wherein said peripheral vein is located in an antecubital fossa.

36. The method of claim 35, wherein said step of intravenously injecting is performed in both antecubital fossae.

37. A method for generating a digital angiographic image of a vascular structure of interest using an intravenous injection comprising the steps of:

intravenously injecting a contrast solution such that it reaches said vascular structure of interest;

scanning said vascular structure of interest with a radiation cone-beam scanner including a two-dimensional detector to acquire first and second sets of nonsubtraction two-dimensional projections;

generating a three-dimensional reconstruction matrix of said vascular structure of interest using data signals generated by said two-dimensional detector; and generating a three-dimensional image of said vascular structure of interest using said three-dimensional reconstruction matrix;

wherein said step of intravenously injecting is performed at a vena cava near a right atrium.

38. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector to acquire first and second sets of nonsubtraction two-dimensional projections;

generating a three-dimensional reconstruction matrix of said vascular structure of interest using data signals generated by said two-dimensional detector; and generating a three-dimensional image of said vascular structure of interest using said three-dimensional reconstruction matrix;

wherein said step of intravenously injecting is performed through a peripheral vein.

39. The method of claim 38, wherein said peripheral vein is located in an antecubital fossa.

40. The method of claim 39, wherein said step of intravenously injecting is performed in both antecubital fossae.

41. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said step of scanning comprises forming subtraction projections.

42. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein said step of scanning comprises forming nonsubtraction projections.

43. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein:
said radiation is x-rays; and
said three-dimensional reconstruction matrix is an x-ray linear attenuation coefficient data matrix.

44. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector to acquire first and second sets of nonsubtraction two-dimensional projections;

generating a three-dimensional reconstruction matrix of said vascular structure of interest using data signals generated by said two-dimensional detector; and generating a three-dimensional image of said vascular structure of interest using said three-dimensional reconstruction matrix;

wherein said three-dimensional reconstruction matrix is an x-ray linear attenuation coefficient data matrix.

45. A method for generating a digital angiographic image of a vascular structure of interest using an intravenous injection, comprising the steps of:

intravenously injecting a contrast solution such that it reaches said vascular structure of interest;

scanning said vascular structure of interest with a radiation cone-beam scanner including a two-dimensional detector to acquire first and second sets of nonsubtraction two-dimensional projections;

generating a three-dimensional reconstruction matrix of said vascular structure of interest using data signals generated by said two-dimensional detector; and generating a three-dimensional image of said vascular structure of interest using said three-dimensional reconstruction matrix;

wherein:

said data signals comprise circular projection signals and arc projection signals;

said two-dimensional detector defines a detector plane and has a local detector coordinate system with an origin, a Radon plane intersecting the detector plane to define a line of intersection, the origin and the line of intersection being connected by a p axis which is perpendicular to the line of intersection; and said three-dimensional reconstruction matrix is generated by rebinning said pre-weighted cone-beam circular and arc projection signals according to the following equations, where D is a radius of the circular orbit, $(\theta, \phi, \rho)$ is a given point in Radon space, p is a perpendicular distance from the origin to the line of intersection measured along the p axis, $\alpha$ is an angular orientation of the p axis relative to the local detector coordinate system, $\beta$ is an angle of rotation of said scanner relative to a plane of said circular orbit, and $\beta_1$ and $\beta_2$ are two points of intersection of the Radon plane with the circular orbit:

(a) for said circular projection signals:

(i) for $\beta_1$:

$$p = \frac{D|\rho|}{\sqrt{D^2 - \rho^2}},$$

$$\alpha = \begin{cases} \sin^{-1}\left(\frac{D\cos\theta}{\sqrt{D^2-\rho^2}}\right) & \text{for } \rho \geq 0, \\ -\sin^{-1}\left(\frac{D\cos\theta}{\sqrt{D^2-\rho^2}}\right) & \text{for } \rho < 0, \end{cases}$$

(ii) for $\beta_2$:

$$p = -\frac{D|\rho|}{\sqrt{D^2 - \rho^2}},$$

$$\alpha = \begin{cases} -\sin^{-1}\left(\frac{D\cos\theta}{\sqrt{D^2-\rho^2}}\right) & \text{for } \rho \geq 0, \\ \sin^{-1}\left(\frac{D\cos\theta}{\sqrt{D^2-\rho^2}}\right) & \text{for } \rho < 0, \end{cases}$$

(b) for said arc projection signals:

$$p = \frac{D\rho}{\sqrt{D^2 - \rho^2}},$$

$$\alpha = \sin^{-1}\left(\frac{\frac{D}{\sqrt{D^2-\rho^2}}\sin\theta\cos\varphi - \frac{\rho}{\sqrt{D^2-\rho^2}}\cos\beta}{\sin\beta}\right).$$

46. Apparatus for performing intravenous tomographic digital angiography of a region of a patient which has received a contrast solution, comprising:

a moveable support on which said patient is placed;

a gantry frame which rotates around said patient;

a cone-beam x-ray source and a two-dimensional detector mounted 180° apart from each other on said gantry frame for synchronous rotation with said gantry frame;

means for acquiring data signals from said two-dimensional detector and for generating three-dimensional angiography images from said acquired data; and means for moving said patient table away from a plane perpendicular to said movable support to acquire line projections.

47. A method for generating a digital angiographic image of a vascular structure of interest using an intravenous injection comprising the steps of:

intravenously injecting a contrast solution such that it reaches said vascular structure of interest;

scanning said vascular structure of interest with a radiation cone-beam scanner including a two-dimensional detector;

generating a three-dimensional reconstruction matrix of said vascular structure of interest using data signals generated by said two-dimensional detector; and generating a three-dimensional image of said vascular structure of interest using said three-dimensional reconstruction matrix;

wherein:

said data signals comprise circular projection signals and arc projection signals said two-dimensional detector defines a detector plane and has a local detector coordinate system with an origin, a Radon plane intersecting the detector plane to define a line of intersection, the origin and the line of intersection being connected by a p axis which is perpendicular to the line of intersection; and said three-dimensional reconstruction matrix is generated by rebinning said pre-weighted cone-beam circular and arc projection signals according to the following equations, where D is a radius of the circular orbit, $(\theta, \phi, \rho)$ is a given point in Radon space, p is a perpendicular distance from the origin to the line of intersection measured along the p axis, $\alpha$ is an angular orientation of the p axis relative to the local detector coordinate system, $\beta$ is an angle of rotation of said scanner relative to a plane of said circular orbit, and $\beta_1$ and $\beta_2$ are two points of intersection of the Radon plane with the circular orbit:

(a) for said circular projection signals:

(i) for $\beta_1$:

$$p = \frac{D|\rho|}{\sqrt{D^2 - \rho^2}},$$

$$\alpha = \begin{cases} \sin^{-1}\left(\frac{D\cos\theta}{\sqrt{D^2-\rho^2}}\right) & \text{for } \rho \geq 0, \\ -\sin^{-1}\left(\frac{D\cos\theta}{\sqrt{D^2-\rho^2}}\right) & \text{for } \rho < 0, \end{cases}$$

(ii) for $\beta_2$:

$$p = -\frac{D|\rho|}{\sqrt{D^2 - \rho^2}},$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0, \end{cases}$$

(b) for said arc projection signals:

$$p = \frac{D\rho}{\sqrt{D^2 - \rho^2}},$$

$$\alpha = \sin^{-1}\left(\frac{\frac{D}{\sqrt{D^2 - \rho^2}}\sin\theta\cos\varphi - \frac{\rho}{\sqrt{D^2 - \rho^2}}\cos\beta}{\sin\beta}\right).$$

* * * * *